US009750804B2

(12) United States Patent
Tsai et al.

(10) Patent No.: US 9,750,804 B2
(45) Date of Patent: Sep. 5, 2017

(54) ALPHA-ENOLASE SPECIFIC ANTIBODIES AND METHOD OF USE IN IMMUNE DISEASES

(71) Applicants: Development Center for Biotechnology, New Taipei (TW); National Health Research Institutes, Miaoli County (TW)

(72) Inventors: Shih-Chong Tsai, New Taipei (TW); Mingl Chang, New Taipei (TW); Ta-Tung Yuan, New Taipei (TW); Shih-Chi Tseng, New Taipei (TW); Shyi-Jou Chen, New Taipei (TW); Wei-Tso Chia, New Taipei (TW); Hsin-Yun Wang, New Taipei (TW); Neng-Yao Shih, Miaoli County (TW); Ko-Jiunn Liu, Miaoli County (TW); Li-Tzong Chen, Miaoli County (TW)

(73) Assignees: Development Center for Biotechnology, New Taipei (TW); National Health Research Institutes, Miaoli County (TW)

( * ) Notice: Subject to any disclaimer, the term of this patent is extended or adjusted under 35 U.S.C. 154(b) by 0 days.

(21) Appl. No.: 14/580,127

(22) Filed: Dec. 22, 2014

(65) Prior Publication Data

US 2015/0175710 A1    Jun. 25, 2015

Related U.S. Application Data

(60) Provisional application No. 61/919,391, filed on Dec. 20, 2013.

(51) Int. Cl.
| | | |
|---|---|---|
| C07K 16/28 | (2006.01) | |
| A61K 39/39 | (2006.01) | |
| B63B 15/02 | (2006.01) | |
| A61K 39/395 | (2006.01) | |
| C07K 16/40 | (2006.01) | |
| B63B 1/12 | (2006.01) | |
| B63H 9/08 | (2006.01) | |
| B63B 15/00 | (2006.01) | |
| A61K 39/00 | (2006.01) | |

(52) U.S. Cl.
CPC .......... *A61K 39/39* (2013.01); *A61K 39/3955* (2013.01); *B63B 1/121* (2013.01); *B63B 15/02* (2013.01); *B63H 9/08* (2013.01); *C07K 16/40* (2013.01); *A61K 2039/505* (2013.01); *B63B 2001/123* (2013.01); *B63B 2015/005* (2013.01); *C07K 2317/34* (2013.01); *C07K 2317/76* (2013.01); *C07K 2317/92* (2013.01)

(58) Field of Classification Search
CPC ........ C07K 16/18; C07K 16/22; C07K 16/24; C07K 16/3023; C07K 14/705; C07K 14/4748
See application file for complete search history.

(56) References Cited

U.S. PATENT DOCUMENTS

| | | | | |
|---|---|---|---|---|
| 4,760,078 | A * | 7/1988 | Yamamoto | C07D 339/04 514/441 |
| 8,449,881 | B2 * | 5/2013 | Leu | C07K 16/40 424/130.1 |
| 2003/0096733 | A1 | 5/2003 | Ny et al. | |
| 2007/0077583 | A1 | 4/2007 | Georges et al. | |
| 2007/0172487 | A1 * | 7/2007 | Shih | C07K 16/3023 424/155.1 |
| 2008/0233185 | A1 | 9/2008 | Joshi et al. | |
| 2011/0182907 | A1 | 7/2011 | Leu et al. | |

FOREIGN PATENT DOCUMENTS

WO     2010/032899 A2    3/2010

OTHER PUBLICATIONS

PCT International Preliminary Report on Patentability (IPRP) and Written Opinion dated Jun. 21, 2016, issued by the International Bureau of WIPO in related International Application No. PCT/US2014/071844 (8 pages).
International Search Report and Written Opinion mailed Apr. 29, 2015, by the International Search Authority in corresponding International Application No. PCT/US14/71844 (13 pages).
Offcial Action issued May 7, 2015, by the Taiwan Patent Office in related Taiwan Patent Application No. TW-103144366, with partial English translation (5 pages).
Wygreck, Malgorzata, et al., "Enolase-1 promotes plasminogen-mediated recruitment of monocytes to the acutely inflamed lung"; Blood, vol. 113, No. 22 (2009); ISSN 0006-4971, online ISSN 1528-0020; doi: 10.1182/ blood-2008-08-170837; pp. 5588-5598.
Diaz-Ramos, Angels, et al., "Alpha-Enolase, a Multifunctional Protein: Its Role on Pathophysiological Situations"; Journal of Biomedicine and Biotechnology, vol. 2012, Article ID 156795; Epub. Oct. 14, 2012; doi: 10.1155/2012/156795; pp. 1-12.

* cited by examiner

*Primary Examiner* — Lorraine Spector

(57) ABSTRACT

A method for treating an inflammatory disease or an immune disorder includes administering to a subject in need of such treatment an antagonist against ENO1. The antagonist binds ENO1 and inhibits ENO1 plasminogen receptor activity. The antagonist may be an anti-human ENO1 antibody, or an scFv, Fab, or F(ab)₂ fragment thereof, that specifically binds to human ENO1 (GenBank: AAH50642.1) for the treatment of an inflammatory disease or an immune disorder, which may be multiple sclerosis, rheumatoid arthritis, Crohn's disease, ulcerative colitis, systemic Lupus erythematosus, chronic obstructive pulmonary disease (COPD), asthma, allergy, psoriasis, type 1 diabetes mellitus, artherosclerosis or osteoporosis.

15 Claims, 32 Drawing Sheets

FIG. 7C (Continued)

TABLE I-US-00002 Mutant KD

| Mutant | KD | Mutant | KD | Mutant | KD |
|---|---|---|---|---|---|
| Wild type | 4.43±0.65 × 10⁻¹⁰ | A300 | 6.33±2.57 × 10⁻⁸ | A301 | Non-detected |
| A302 | 3.45±0.28 × 10⁻¹⁰ | A305 | 3.31±0.50 × 10⁻¹⁰ | A306 | 4.65±2.42 × 10⁻¹⁰ |
| A309 | 5.63±2.67 × 10⁻⁹ | A326 | 7.87±1.35 × 10⁻¹⁰ | A330 | Non-detected |
| A333 | 4.13±1.09 × 10⁻¹⁰ | A334 | 1.07±4.39 × 10⁻⁷ | A335 | 9.57±3.72 × 10⁻⁹ |

FIG. 7D $^{296}$FDQDDWGAWQKFTASAGIQVVGDDLTVTNPKRIAKAVNEKS$^{336}$ SEQ ID NO:39

SEQ ID: 40     SEQ ID: 41

FIG.12A

| | | | | | | | | | |
|---|---|---|---|---|---|---|---|---|---|
| 15F8 | 1.552 | 12D9 | 1.563 | 4A7 | 1.968 | 17G10 | 1.780 | 7G6 | 1.580 | 6C4 | 2.119 |
| 17A11 | 1.683 | 13D8 | 1.522 | 4B2 | 1.768 | 18D11 | 1.747 | 9A4 | 1.660 | 6D6 | 2.068 |
| 17C9 | 1.458 | 11B4 | 1.642 | 4C5 | 1.655 | 18H3 | 1.706 | 9C2 | 1.484 | 6E2 | 1.738 |
| 15H4 | 1.547 | 12B10 | 1.363 | 4D5 | 2.008 | 10F4 | 1.271 | 9E1 | 1.686 | 6F5 | 1.851 |
| 16D4 | 1.514 | 12E8 | 1.784 | 4E3 | 2.215 | 11B10 | 1.528 | 22B4 | 1.446 | 6H5 | 1.879 |
| 17B7 | 1.749 | 13G2 | 1.654 | 4F3 | 2.079 | 12D4 | 1.471 | 22C8 | 1.912 | 1C6 | 1.884 |
| 17E10 | 1.499 | 11A10 | 1.468 | 4F5 | 1.749 | 14D2 | 1.528 | 22C11 | 1.57 | 1E2 | 1.657 |
| 16A2 | 1.768 | 12C10 | 1.496 | 4F6 | 1.945 | 11A3 | 1.507 | 22F3 | 1.587 | 1F5 | 1.609 |
| 16H3 | 1.685 | 12F4 | 1.342 | 5A12 | 2.193 | 12C1 | 1.447 | 22F5 | 1.58 | 2D2 | 1.872 |
| 18G4 | 1.602 | 7C9 | 1.423 | 5D6 | 2.052 | 2D8 | 1.994 | 2G9 | 1.725 | 3B1 | 1.685 |
| 16B5 | 1.772 | 7D5 | 1.490 | 5E1 | 1.766 | 2F3 | 2.038 | 3A2 | 1.758 | 3B11 | 1.655 |
| 17A10 | 1.573 | 7E5 | 1.465 | 6B11 | 2.114 | 2G4 | 1.586 | 3A5 | 1.812 | 3C8 | 1.723 |
| 3D1 | 1.698 | 3H8 | 2.014 | 17H3 | 2.007 | | | | | | |

FIG.12B

| ID | Value | ID | Value | ID | Value | ID | Value |
|---|---|---|---|---|---|---|---|
| 15F8 | 1.642 | 12D9 | 0.486 | 4A7 | 1.765 | 17G10 | 0.846 | 7G6 | 0.585 | 6C4 | 1.794 |
| 17A11 | 1.705 | 13D8 | 1.308 | 4B2 | 1.421 | 18D11 | 1.239 | 9A4 | 1.254 | 6D6 | 1.562 |
| 17C9 | 0.825 | 11B4 | 1.213 | 4C5 | 1.357 | 18H3 | 1.444 | 9C2 | 0.927 | 6E2 | 1.943 |
| 15H4 | 1.433 | 12B10 | 1.449 | 4D5 | 1.465 | 10F4 | 0.918 | 9E1 | 1.985 | 6F5 | 2.008 |
| 16D4 | 1.694 | 12E8 | 1.103 | 4E3 | 1.928 | 11B10 | 1.125 | 22B4 | 1.218 | 6H5 | 1.656 |
| 17B7 | 1.862 | 13G2 | 1.458 | 4F3 | 1.540 | 12D4 | 1.336 | 22C8 | 1.785 | 1C6 | 1.575 |
| 17E10 | 1.582 | 11A10 | 1.051 | 4F5 | 1.233 | 14D2 | 1.780 | 22C11 | 1.690 | 1E2 | 1.668 |
| 16A2 | 1.246 | 12C10 | 1.333 | 4F6 | 1.569 | 11A3 | 1.619 | 22F3 | 1.345 | 1F5 | 1.911 |
| 16H3 | 1.456 | 12F4 | 0.899 | 5A12 | 2.216 | 12C1 | 1.408 | 22F5 | 1.511 | 2D2 | 1.563 |
| 18G4 | 1.805 | 7C9 | 1.644 | 5D6 | 2.258 | 2D8 | 1.550 | 2G9 | 1.923 | 3B1 | 1.768 |
| 16B5 | 1.667 | 7D5 | 1.675 | 5E1 | 1.340 | 2F3 | 1.643 | 3A2 | 1.680 | 3B11 | 1.509 |
| 17A10 | 1.302 | 7E5 | 0.582 | 6B11 | 0.445 | 2G4 | 0.912 | 3A5 | 1.482 | 3C8 | 1.237 |
| 3D1 | 1.155 | 3H8 | 2.043 | 17H3 | 1.698 | | | | | | |

SEQUENCE LISTING

```
<160> NUMBER OF SEQ ID NOS: 41

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
ggatccgcag caaacttcag ggaagccatg                                          30

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
ggatcctcga agatcccttt gaccaggatg                                          30

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
tcaggctgaa aatctctcat ccgc                                                24

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
ggatcctatc tattctcaag atccatgcc                                           29
```

<210> SEQ ID NO 5
<211> LENGTH: 33
<212> TYPE: DNA
<213> ORGANISM: Artificial Sequence
<220> FEATURE:
<223> OTHER INFORMATION: Synthetic

<400> SEQUENCE: 5
ctcgaggtca tggtgtctca tcgttcgctc gag        33

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
gtaaacaacg acggcgag        18

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
caggaaacag ctatgac        17

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
ctcgagaggg atcttcgata gacaccactg gg        32

<210> SEQ ID NO 9
<211> LENGTH: 30
<212> TYPE: DNA
<213> ORGANISM: Artificial Sequence
<220> FEATURE:
<223> OTHER INFORMATION: Synthetic

<400> SEQUENCE: 9
ctcgagctac ctggattcct gcactggctg        30

<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
ctcgagactt ctcgttcacg gccttggcga tc        32

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
ctcgagactt ctcgttcacg gccttggcga tcc       33

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
ctcgagcagt ctcccccgaa cgatgagaca cc        32

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
ctcgagcacc agtcttgatc tgcccagtgc ac        32

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14 gatcccttg accaggatgc tggggagct tggcag      36

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
ctgccaagct ccccaggcat cctggtcaaa gggatc    36

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
ccctttgacc aggatgacgc gggagcttgg cagaag    36

<210> SEQ ID NO 17
<211> LENGTH: 36
<212> TYPE: DNA
<213> ORGANISM: Artificial Sequence
<220> FEATURE:
<223> OTHER INFORMATION: Synthetic

<400> SEQUENCE: 17
cttctgccaa gctcccgcgt catcctggtc aaaggg    36

<210> SEQ ID NO 18
<211> LENGTH: 37

-continued

<212> TYPE: DNA
<213> ORGANISM: Artificial Sequence
<220> FEATURE:
<223> OTHER INFORMATION: Synthetic

<400> SEQUENCE: 18
ctttgaccag gatgactggg cagcttggca gaagttc         37

<210> SEQ ID NO 19
<211> LENGTH: 37
<212> TYPE: DNA
<213> ORGANISM: Artificial Sequence
<220> FEATURE:
<223> OTHER INFORMATION: Synthetic

<400> SEQUENCE: 19
gaacttctgc caagctgccc agtcatcctg gtcaaag         37

<210> SEQ ID NO 20
<211> LENGTH: 36
<212> TYPE: DNA
<213> ORGANISM: Artificial Sequence
<220> FEATURE:
<223> OTHER INFORMATION: Synthetic

<400> SEQUENCE: 20
gactggggag cttgggcgaa gttcacagcc agtgca          36

<210> SEQ ID NO 21
<211> LENGTH: 36
<212> TYPE: DNA
<213> ORGANISM: Artificial Sequence
<220> FEATURE:
<223> OTHER INFORMATION: Synthetic

<400> SEQUENCE: 21
tgcactggct gtgaacttcg cccaagctcc ccagtc          36

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22
ggggagcttg gcaggcgttc acagccagtg cagg            34

<210> SEQ ID NO 23
<211> LENGTH: 34
<212> TYPE: DNA
<213> ORGANISM: Artificial Sequecne
<220> FEATURE:
<223> OTHER INFORMATION: Synthetic

<400> SEQUENCE: 23
cctgcactgg ctgtgaacgc ctgccaagct cccc            34

<210> SEQ ID NO 24
<211> LENGTH: 36
<212> TYPE: DNA
<213> ORGANISM: Artificial Sequence
<220> FEATURE:
<223> OTHER INFORMATION: Synthetic

<400> SEQUENCE: 24
ggcagaagtt cacaggcagt gcaggaatcc aggtag                                36

<210> SEQ ID NO 25
<211> LENGTH: 36
<212> TYPE: DNA
<213> ORGANISM: Artificial Sequence
<220> FEATURE:
<223> OTHER INFORMATION: Synthetic

<400> SEQUENCE: 25
ctacctggat tcctgcactg cctgtgaact tctgcc                                36

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
tcacagtgac caacccagcg aggatcgcca aggcc                                 35

<210> SEQ ID NO 27
<211> LENGTH: 35
<212> TYPE: DNA
<213> ORGANISM: Artificial Sequence
<220> FEATURE:
<223> OTHER INFORMATION: Synthetic

<400> SEQUENCE: 27
gccttggcga tcctcgctgg gttggtcact gtgag                                 35

<210> SEQ ID NO 28
<211> LENGTH: 37
<212> TYPE: DNA
<213> ORGANISM: Artificial Sequence
<220> FEATURE:
<223> OTHER INFORMATION: Synthetic

<400> SEQUENCE: 28
caacccaaag aggatcgccg cggccgtgaa cgagaag                               37

<210> SEQ ID NO 29
<211> LENGTH: 37
<212> TYPE: DNA
<213> ORGANISM: Artificial Sequence
<220> FEATURE:
<223> OTHER INFORMATION: Synthetic

<400> SEQUENCE: 29
cttctcgttc acggccgcgg cgatcctctt tgggttg                               37

<210> SEQ ID NO 30
<211> LENGTH: 37
<212> TYPE: DNA
<213> ORGANISM: Artificial Sequence
<220> FEATURE:
<223> OTHER INFORMATION: Synthetic

<400> SEQUENCE: 30
gaggatcgcc aaggccgtgg ccgagaagtc ctgcaac                               37

<210> SEQ ID NO 31
<211> LENGTH: 37
<212> TYPE: DNA
<213> ORGANISM: Artificial Sequence

```
<220> FEATURE:
<223> OTHER INFORMATION: Synthetic

<400> SEQUENCE: 31
gttgcaggac ttctcggcca cggccttggc gatcctc                              37

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
gatcgccaag gccgtgaacg cgaagtcctg caactg                               36

<210> SEQ ID NO 33
<211> LENGTH: 37
<212> TYPE: DNA
<213> ORGANISM: Artificial Sequence
<220> FEATURE:
<223> OTHER INFORMATION: Synthetic

<400> SEQUENCE: 33
gcagttgcag gacttcgcgt tcacggcctt ggcgatc                              37

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
gccaaggccg tgaacgaggc gtcctgcaac tgcctc                               36

<210> SEQ ID NO 35
<211> LENGTH: 36
<212> TYPE: DNA
<213> ORGANISM: Artificial Sequence
<220> FEATURE:
<223> OTHER INFORMATION: Synthetic

<400> SEQUENCE: 35
gaggcagttg caggacgcct cgttcacggc cttggc                               36

<210> SEQ ID NO 36
<211> LENGTH: 37
<212> TYPE: DNA
<213> ORGANISM: Artificial Sequence
<220> FEATURE:
<223> OTHER INFORMATION: Synthetic

<400> SEQUENCE: 36
caaggccgtg aacgcggcgt cctgcaactg cctcctg                              37

<210> SEQ ID NO 37
<211> LENGTH: 37
<212> TYPE: DNA
<213> ORGANISM: Artificial Sequence
<220> FEATURE:
<223> OTHER INFORMATION: Synthetic

<400> SEQUENCE: 37
caggaggcag ttgcaggacg ccgcgttcac ggccttg                              37
```

```
<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
gcaaggggca ccagtcttga tctg                                              24

<210> SEQ ID NO 39
<211> LENGTH: 82
<212> TYPE: PRT
<213> ORGANISM: Homo sapiens

<400> SEQUENCE: 39

Phe Asp Gln Asp Asp Trp Gly Ala Trp Gln Lys Phe Thr Ala Ser Ala
1               5                   10                  15

Gly Ile Gln Val Val Gly Asp Asp Leu Thr Val Thr Asn Pro Lys Arg
            20                  25                  30

Ile Ala Lys Ala Val Asn Glu Lys Ser Phe Asp Gln Asp Asp Trp Gly
        35                  40                  45

Ala Trp Gln Lys Phe Thr Ala Ser Ala Gly Ile Gln Val Val Gly Asp
    50                  55                  60

Asp Leu Thr Val Thr Asn Pro Lys Arg Ile Ala Lys Ala Val Asn Glu
65                  70                  75                  80

Lys Ser

<210> SEQ ID NO 40
<211> LENGTH: 14
<212> TYPE: PRT
<213> ORGANISM: Homo sapiens

<400> SEQUENCE: 40

Phe Asp Gln Asp Asp Trp Gly Ala Trp Gln Lys Phe Thr Ala
1               5                   10

<210> SEQ ID NO 41
<211> LENGTH: 11
<212> TYPE: PRT
<213> ORGANISM: Homo sapiens

<400> SEQUENCE: 41

Lys Arg Ile Ala Lys Ala Val Asn Glu Lys Ser
1               5                   10
```

ALPHA-ENOLASE SPECIFIC ANTIBODIES AND METHOD OF USE IN IMMUNE DISEASES

CROSS REFERENCE TO RELATED APPLICATIONS

The claims the benefits of Provisional Application No. 61/919,391, filed on Dec. 20, 2013, the disclosure of which is incorporated by reference in its entirety.

BACKGROUND OF INVENTION

Field of the Invention

The present invention relates to treatments of multiple sclerosis, rheumatoid arthritis, Crohn's disease, ulcerative colitis, systemic Lupus erythematosus, and related immune disorders, including chronic obstructive pulmonary disease (COPD), asthma, allergy, psoriasis, type 1 diabetes mellitus, and osteoporosis, by means of specific antibodies to alpha-Enolase.

Multiple sclerosis (MS) is a chronic inflammatory disease of the central nervous system. In multiple sclerosis, myelin sheaths of nerve fibers are destroyed, i.e. the nerve fibers are demyelinated by auto antibodies. The symptoms of multiple sclerosis are relatively unspecific and, for example, relapse and remission of fatigue, numbness, gait and coordination problems, bowel/bladder dysfunction, cognitive dysfunction and pains. So far, causes and pathophysiology are poorly understood and may be caused by genetic background, vitamin D deficiency and geography. Prevalence of MS is variable geographically. Western European and North American have the highest epidemic rates in the world with 100 symptomatic MS patients per 100,000 in the U.S. and 118/100,000 in England. The prevalence in Japan and Taiwan is 8.57/100,00 and 1.9/100,000, respectively (Amino, M J. et al. (2009) New York: McGraw Hill Medical., pp. 848-911; Tsai, C-P. et al. (2004), Chinese Med. Assoc., 67: 500-505). Genetic background is also involved in the pathogenesis of MS. If a family member is affected by MS, the risk for their relatives to develop MS is proportional to the genetic similarity between themselves and the affected person. Among the environmental factors, Vitamin D and Eptein-Barr virus infection are confirmed to be factors that link to MS. Recently, Herpes viruses type V and VI are proposed to be involved in MS in Taiwan. Early in the understanding of MS pathology, it was thought that myelin-specific CD4+T lymphocytes migrate from the blood to brain, bind to antigenic peptides presented by antigen presenting cells (including microglial in the brain), clonally expand, attack and damage oligodendrocytes, and destroying myelin. Recent hypothesis suggests that myelin CD+4 T-cells are only involved in the early phase of MS. Circulation monocytes, induced by MCP-1 in CNS, are responsible for the mid and late phase of disease progression. Mice deficient in the chemokine receptor CCR2, of which ligand is MCP-1, are resistant to experimental autoimmune encephalomyelitis (EAE). When CCRC2 knock-out mice are transfused with different amounts of monocytes from EAE-induced CCRC2+ mice, clinical scores of recipient mice are proportional to the amounts of transfused monocytes from the donor EAE mice. This result suggests that monocytes are very important for the EAE disease progression.

Until now, no satisfactory therapy of multiple sclerosis has been found. There are 8 drugs approved by U.S. FDA to treat MS patients. Rebif, Avonex, betaferon, and Extavia are different types of β-interferons, which are immunomodulators. Copaxon is a myelin analogy functioning as a decoy receptor for Th1 CD4+ antigen. Gilenya is a spingosine 1-phosphate (S1P-1) receptor modulator with a structure closely related to sphingosine. Gilenya acts as a functional antagonist at lymphocytic S1P, and the immunomodulating effects of Gilenya are likely due to inhibition of egress of antigen-specific T-cells from draining lymph nodes. Tysabri is a monoclonal antibody against the extracellular matrix receptor integrin (α4β1), which is important for the migration of leukocytes. Laquinimod is a NFκB-mediated inflammatory pathway inhibitor; the effective cells include T-cells, B-cells and dendritic cells. Tecfidera (dimethyl fumarate BG12) is a Nrf2 transcription pathway inhibitor, and it prevents immune cells from secreting cytokines and epithelial cells from expressing CD 62E. Mitoxantrone is an analogy of anthracenedion, which is toxic to activated immune cells. Even though some of them are every effective, these drugs only lead to decreased frequency and intensity of the acute phases of the disease. They always have some side effects, for example infections for β-interferons related drugs and progressive multifocal leukoencephalopathy for Tysabri.

Rheumatoid arthritis (RA) is a chronicle inflammatory disease that affects patients' joints. Symptoms of RA include pains, swellings, stiffness, and deformations in joints. Patients always feel fever and fatigue. The etiology of RA is not fully understood. The disease starts from auto antibodies against patients' connective tissues, followed by infiltration of leukocytes including monocytes, macrophages and neutrophils. Then, lymphocytes erode and invade bones and soft tissues of joints. Traditional therapeutic drugs of RA are referred to as antirheumatics, including, for example, methotrexate and lefunomide. Sometimes steroids are used. Recently, more effective biologics, such as Remicade™ and Humira™, which are antibodies against TNF-alpha, or Enbrel, which is a decoy receptor of TNF-alpha, or Anakinra™, which is a receptor antagonist of IL-1, can be administrated. Even though these drugs are effective, side effects, for example, infections and fevers can be seen. Still, in many cases, it is not possible to satisfactorily treat the disease and to avoid damages to joints, which can even result in immobilization.

In both diseases (MS and RA), data in the literatures support that inflammatory blood monocytes and macrophages are involved in the progression of both immune diseases.

Alpha-enolase (enolase-1 or ENO1) is a multiple functional protein, which was first found as a key enzyme in the glycolysis pathway. Under normal conditions, ENO1 is expressed in the cytosol. However, recent data in the literatures support the notion that ENO1 can express on the cell surfaces as a plasminogen receptor in many cancer cells and activated hematopoietic cells, such as neutrophils, lymphocytes and monocytes. It is known that the up-regulation of plasminogen receptor proteins induces the cascade responses of UPAS (urokinase plasminogen activation signal) and results in extracellular matrix degradation. As a consequence, it results in increased metastasis of cancer cells and infiltration of immune cells. Inflammatory stimuli, for example LPS, up-regulate ENO1 cell-surface expression on human blood monocytes and U937 monocytic cells by post translational modification and translocation to cell surface.

It is believed the translocation of ENO1 is regulated by the MAP kinase signal transduction pathway. This implies that increases in the expression of ENO1 on cell surface may play an important role in the inflammatory diseases. Auto antibodies against ENO1 have been found in variable autoimmune and inflammatory diseases, including Lupus erythematousus, systemic sclerosis, Behcet disease, ulcerative, and Crohn's disease. Saulot et al. (Arthritis Aheum., 46:1196-1201(2002)) and Wkui et al. (Clin. Exp. Immunol., 118:445-450 (1999)) studies suggest that 25-66% of RA patients have serum up-regulated levels of antibodies against ENO1. Bae's study (J. Immunology, 189:365-372 (2013)) indicates that when RA patients' PBMCs are treated with an antibody against ENO1 to stimulate the ENO1 plasminogen receptor activity, monocytes and macrophages from the PBMCs produce higher amount of pro-inflammatory mediators, such as TNFα, IL1-α/β, IFN-γ and PGE2 via p38 MAPK and NF-κB pathway. This study suggests that ENO1, by way of its plasminogen receptor activity, plays a key role in the disease progression of RA patients by increasing invasion activities of monocytes and macrophages.

In sum, monocytes with their up-regulated ENO1 expression on cell surfaces as plasminogen receptors to increase invasion activities are very important for the disease progression of MS, RA, and related immune disorders. Therefore, targeting ENO1 on the cell surface of monocytes has a good potential to treat inflammatory diseases, such as MS, RA, Crohn's disease, ulcerative colitis, and systemic Lupus erythematosus, or related immune disorders, such as chronic obstructive pulmonary disease (COPD), asthma, allergy, psoriasis, type 1 diabetes mellitus, artherosclerosis and osteoporosis.

SUMMARY OF INVENTION

Embodiments of the present invention provide new treatments for an inflammatory disease or an immune disorder, such as multiple sclerosis, rheumatoid arthritis, Crohn's disease, ulcerative colitis, systemic Lupus erythematosus, or relative immune disorders, such as chronic obstructive pulmonary disease (COPD), asthma, allergy, psoriasis, type 1 diabetes mellitus, atherosclerosis and osteoporosis.

In accordance with embodiments of the invention, a method for treating an inflammatory disease or an immune disorder, may comprise administering to a subject in need thereof an antagonist against ENO1, wherein the antagonist binds ENO1 and inhibits ENO1 plasminogen receptor activity. The antagonist may be an anti-ENO1 antibody. In addition, the method may further comprise administering an immunomodulator to the subject. An example of air immunomodulator is dimethyl fumarate.

Embodiments of the invention may be accomplished with a medicament containing an antibody that can bind specifically to ENO1 plasminogen receptor for the treatment of multiple sclerosis, rheumatoid arthritis, Crohn's disease, ulcerative colitis, systemic Lupus erythematosus, or relative immune disorders in a subject, and the use of said antibody for the manufacture of a medicament for the treatment of multiple sclerosis, rheumatoid arthritis, Crohn's disease, ulcerative colitis, systemic Lupus erythematosus, or relative immune disorders in a subject, respectively.

In accordance with embodiments of the invention, an antibody, or an scFv, Fab or F(ab)2 fragment thereof, can bind to an epitope on human ENO1 and inhibit ENO1 plasminogen receptor activity, wherein the epitope may be located in a region consisting of the sequence of $^{296}$FDQDDWGAWQKFTASAGIQVVG DDLTVTNPKRI-AKAVNEKS$^{336}$ (SEQ ID NO:39) of human ENO1. In accordance with any of the above embodiments of the invention, the antibody, or the scFv, Fab or F(ab)$_2$ fragment thereof, can bind to an epitope on human ENO1 and inhibit ENO1 plasminogen receptor activity, wherein the epitope may be located in a region consisting of the sequence of $^{296}$FDQDDWGAWQKFTA$^{309}$ (SEQ ID NO:40) or $^{326}$KRI-AKAVNEKS$^{336}$ (SEQ ID NO:41) of human ENO1.

As noted above, Bae's study (J. Immunology, 189:365-372 (2013)) indicates that when RA patients' PBMCs are treated with an antibody against ENO1, the ENO1 plasminogen receptor activity is stimulated, and monocytes and macrophages from the PBMCs would produce higher amount of pro-inflammatory mediators, such as TNFα, IL1-α/β, IFN-γ and PGE2 via p38 MAPK and NF-κB pathway. In contrast to this observation, inventors of this invention surprisingly found that the administration of antibodies directed against ENO1 can effect a clinical improvement of rheumatoid arthritis. That is, it was found that by administering antibodies directed against ENO1 activity instead of activation with the antibody epitope which is different from that chosen by Bae et al., a clinical improvement in an inflammatory disease or immune disorder (such as rheumatoid arthritis) can be achieved. Likewise, it was found that a clinical improvement in multiple sclerosis can be effected. These observations suggest that not every ENO1 antibody has therapeutic effect on immune diseases and this effect is epitope dependent.

Furthermore, it was surprisingly found that a treatment is not only possible during the initiation of the disease in an animal model, but also when explicit clinical symptoms of the disease are already present. This allows for a relatively late therapeutic intervention, among others, as it is required in human clinical practice.

The human ENO1 plasminogen receptor is known to a person skilled in the art (see, GenBank: AAH50642.1 on the Website of the National Institute of Health). This receptor is a plasminogen receptor and exists in two different splicing variants in humans, ENO1 and Myc binding protein. ENO1 is also known as human ENO1, alpha-Enolase, or ENO-1 gene.

The corresponding orthologs of ENO1 from several other species are also known and can easily be determined by a person skilled in the art, for example, by means of sequence searches starting from the human ENO1. In accordance with embodiments of the invention, the term "ENO1" refers to both human and animal (e.g., pets and livestock) ENO1 proteins.

According to the present invention, the term "antibody" is to be understood in a broad sense and, among others, comprises polyclonal, monoclonal and recombinantly produced antibodies including bi-specific antibodies as well as fragments thereof, such as Fv, Fab, and F(ab)2 fragments, wherein the Fv may be single-stranded (single chain). Preferably, the antibody is one of the IgG isotypes. Preferably, the antibody is such that it is not, or only to a low extent, rejected by the immune system of the subject. This can, for example, be achieved by converting antibody regions (e.g., the Fc regions) that are not required for recognizing the antigen (e.g., the ENO1 protein, which is a plasminogen receptor) to sequences derived from antibody sequences of the species of the subject. For example, so called humanized antibodies are known to a person skilled in the art and are particularly suitable for applications in humans. Antibodies that are otherwise modified, e.g. bispecific antibodies (see, for example, Kontermann, R. E. (editor) (2011), Bispecific antibodies, Springer Heidelberg Dordrecht London New York), diabodies, as well as so-called binders or aptamers, which can, for example, be made by means of a peptide backbone or a nucleic acid backbone, for example aRNA, are also intended to be encompassed by the term "antibody" in the context of the present invention. Preferably, antibodies in the context of the present invention have a molecular weight of less than 600 kDa, more preferably of less than 300 kDa, still more preferably of less than 200 kDa, and most preferably of about 150 kDa. Antibody as used herein may also include a chimeric antibody, a human antibody, an affinity matured antibody, which is an antibody that has been subjected to mutation to optimize the binding (affinity). The antibody can also be conjugated to a drug to form an antibody-drug conjugate (ADC). Methods for forming antibody and drug conjugates are well known in the art, for example involving oxidation of carbohydrates on the antibody with sodium periodate to generate aldehydes, which are then reacted with an amine functional group on a drug or a linker attached to a drug.

Methods for the production of suitable polyclonal, monoclonal and recombinant antibodies, including the production of binders and aptamers, are known to a person skilled in the art (see, for example, Jorg Knablein (editor), Modern Biopharmaceuticals, vol. 2, p. 635); see also the Examples described below. For example, the immunization can be carried out by injection of the ENO1 protein. Identification of suitable antibodies is also possible by screening of hybridoma supernatant with the corresponding molecules (antigens). After identification, the antibodies can be produced by methods that are known to a person skilled in the art.

According to embodiments of the present invention, an anti-ENO1 antibody may be EN10 mAb or 7E5 mAb, or an scFv, Fab, or F(ab)2 fragment thereof. The anti ENO1 antibody EN10 mAb and 7E5 mAb can bind to the plasminogen receptor ENO1. Preferably, the antibody binds with a dissociation constant $K_d$ of $10^{-7}$ M or lower, more preferably of $10^{-8}$ M or lower, even more preferably of $10^{-9}$ M or lower, most preferably of $10^{-10}$ M or lower. Preferably, the binding is specific. Specific binding in the context of the present invention means that under physiological conditions (that is, for example, in physiological salt solution, in cell culture or in vivo, preferably in the blood or tissue of the corresponding subject), the antibody binds to ENO1 with at least 10-fold better affinity, preferably 20-fold better affinity, more preferably 50-fold better affinity, most preferably 100-fold better affinity to ENO1, as compared to those of other proteins, in particular, as compared to similar proteins (e.g., as compared to Annexin 2, Histone 2B, CK8, or other plasminogen receptors). However, binding to other proteins may be tolerated as long as it does not interfere with the therapeutic effects of the antibody. Yet, cross-reactivity with orthologous ENO1 plasminogen receptors from other species is possible and can even be advantageous in order to allow for applications of the antibody in several species. Such cross-reactivity is not uncommon and it is known to a person skilled in the art how to determine the cross-reactivity. Further details regarding this matter can also be found in the Examples.

Preferably, an antibody to be used according to embodiments of the invention can inhibit the ENO1 plasminogen receptor activity. Whether an antibody inhibits the ENO1 plasminogen receptor activity can easily be determined. For example, such antibody can decrease plasmin proteinase activity that results from LPS-induced ENO1 plasminogen receptor expression on cells that react by means of ENO1, such as U937 cells. An exemplary assay is described in the Examples below.

Furthermore, inhibition of the ENO1 plasminogen receptor activity can be determined by the fact that inhibition of invasion activity induced by LPS and MCP-1 occurs in cells, e.g. U937. An exemplary assay is described in the Examples below.

Examples for antibodies that are suitable or can resemble starting points for modified antibodies include the monoclonal antibody EN10 mAb and 7E5 mAb. Production of antibody EN10 mAb and 7E5 mAb, as well as their features, is described in the Examples below.

A medicament according to embodiments of the invention may contain antibody EN10 mAb and 7E5 mAb. In addition, the medicament can contain any type of adjuvant, which a person skilled in the art considers acceptable. Such adjuvants can, for example, be carrier substances, such as starch, lactose, fats, stearic acid, alcohol, physiological saline solutions or other additives. In particular, adjuvants that stabilize antibodies and preserve their activities are desirable. The medicament according to embodiments of the invention may also contain antibodies that have other therapeutic molecules conjugated on the antibodies (i.e., antibody-drug conjugates, ADC), methods for making ADC are well known in the art.

Administration of the medicament can be carried out with any known method that can deliver the antibody EN10 mAb and 7E5 contained in the medicament to the target cells, e.g., in particular monocytes, in vitro or in vivo. For example, the medicament can be administered by injection, e.g. intravenously (i.v.), subcutaneously (s.c.), or intraperitoneally (i.p.) in the form of solutions, suspensions, or infusions. However, other modes of administration, such as in microencapsulated form or in the form of implants, are also possible. Preferably, administration of the medicament is carried out such that the antibody can enter into the circulation or into the respective target area. It is also possible to administer directly into the target area, for example, for multiple sclerosis directly into the central nervous system (e.g., the cerebral spinal fluid), for rheumatoid arthritis directly into the affected joints, for inflammatory bowel disease directly into the intestines, for SLE directly in the kidneys, or for other inflammatory diseases directly in the relative organs.

Multiple sclerosis (MS) and rheumatoid arthritis (RA) are known to a person skilled in the art and have already been described in the introduction. The term treatment is also known to a person skilled in the art. In the context of the present invention, a treatment concerns any kind of intervention that results in clinical improvement in a disease or disorder, such as multiple sclerosis, rheumatoid arthritis, Crohn's disease, ulcerative colitis, or systemic Lupus erythematosus or an immune disorder in a subject. A clinical improvement, for example in multiple sclerosis, may be determined by measuring the decrease in neurological deficit, e.g., palsy. In rheumatoid arthritis, a clinical improvement can be determined, for example, by a reduction in the symptoms, such as swelling, inflammation, or the pain. Preferably, an improvement manifests itself in alleviation of clinical symptoms which, for example, correspond to an improvement in EAE score, according to the example, of at least 0.25 unit, preferably 0.5 units, more preferably at least 0.75 unit, more preferably at least 1.0 unit, or most preferably at least 1.3 units. Preferably, the improvement manifests itself in alleviation of clinical symptoms which, for example, corresponds to an improvement in the arthritis score, according to the example, of at least 0.25 unit, preferably at least 0.5unit, more preferably at least 1.0 unit, more preferably at least 2.0 units, or most preferably at least 3.0 units.

For an estimation of clinical improvement in man, many parameters are known as well, for example the clinical score for multiple sclerosis (Avnir, Y. et al., (2011) PLoS ONE.6: 1-13). Furthermore, treatment can, in particular, concern a therapy-refractory multiple sclerosis and/or rheumatoid arthritis, i.e. a form of the respective disease, in which a clinical improvement could not be achieved with the hitherto known agents. In a considerable number of subjects, the course of a disease is such that clinical improvement is no longer possible with known agents. Furthermore, treatment may concern a subject with the respective disease, in which undesired side effects occur to a non-acceptable extent with the hitherto existing treatment methods. The treatment may also concern the respective disease in an advanced stage.

A subject in accordance with embodiments of the present invention may be a vertebrate, preferably a mammal. A mammal can, for example, be a rodent (e.g. mouse, rat or rabbit), a pig, a dog, a cat or primate. Preferably, the mammal is a primate (for example, a macaque or a common marmoset or a human). Particularly preferred, the subject is a human.

Usually, an effective dose is determined for the administration of the medicament. The term "an effective dose" and the determination of the effective dose is known to a person skilled in the art. Furthermore, a person skilled in the art can consult the information provided herein for determining an effective dose. A dose is understood to be effective when it leads to clinical improvement in the disease being treated. In particular, in the context of the present invention, a dose of the medicament which effects an alleviation of the symptoms of multiple sclerosis, rheumatoid arthritis, Crohn's disease, ulcerative colitis, systemic Lupus erythematosus or an immune disorder in a subject is understood to be an effective dose. An effective dose is, for example, a dose which is chosen such that at least 20%, preferably at least 30%, more preferably at least 40%, most preferably at least 50% of invasion activities of the ENO1-expressing monocytes in the peripheral blood are inhibited.

Preferably, an effective dose of the medicament is chosen such that it resembles the lowest dose that provides for satisfactory treatment of multiple sclerosis, rheumatoid arthritis, Crohn's disease, ulcerative colitis, systemic Lupus erythematosus or an immune disorder. A particularly suitable effective dose can be determined by continuing to increase the doses in a test series until the desired ratio of effect to undesired side effects is reached. In the context of the present invention, this will, for example, be the case when the disease being treated is no longer further improved clinically upon a further increase in the dose (as the case may be, is even aggravated) and/or when the undesired side effects relative to the therapeutic effect are no longer acceptable.

Moreover, the present invention relates to a medicament containing an antibody capable of inhibiting invasion activity of monocytes in multiple sclerosis, rheumatoid arthritis, Crohn's disease, ulcerative colitis, systemic Lupus erythematosus or an immune disorder in a subject and the use of said antibody for the manufacture of a medicament for the treatment of multiple sclerosis, rheumatoid arthritis, Crohn's disease, ulcerative colitis, systemic Lupus erythematosus or an immune disorder in a subject.

All preferred embodiments and variants of the invention and definitions illustrated in this description evidently also relate to all of aforementioned medicaments and uses in a corresponding manner.

In the context of the present invention, it was found that the administration of an antibody, which is able to inhibit the plasminogen receptor ENO1, can affect the invasion activity of ENO1-expressing monocytes.

The present inventors assume that the treatment of multiple sclerosis, rheumatoid arthritis, Crohn's disease, ulcerative colitis, systemic Lupus erythematosus or an immune disorder preferentially occurs via a compromise of plasminogen receptor activity of ENO1-expressing inflammatory monocytes.

In the context of the present invention, inhibition of plasminogen receptor activity of ENO1-expressing inflammatory monocytes is understood to result in the compromise of the invasion activity of the corresponding monocytes.

The mechanism of inhibition of plasminogen receptor activity can be influenced by the design of the antibody. Preferably, the inhibition is effected by a mechanism of compromising the UPAS (urokinase plasminogen activation signal) activity. The inhibition based on UPAS can, for example, be mediated via ENO1 protein. ENO1 antibody makes it possible that the migration of monocytes to inflammatory tissues is held back.

Inhibition of invasion activity with the help of an antibody of the invention can be achieved in various species. For instance, the monocyte populations of mouse and man are similar. In mouse, a dichotomy of the blood monocytes into inflammatory (CD11b+ CCR2+ GR1+ CD62L+ CX3CR1low) and non-inflammatory (CD11b+ CCR2$^-$ GR1$^-$ CD62L$^-$ CX3CR1high) monocytes has been demonstrated (Geissmann F. et al. (2003), Immunity, 19: 71-82). In humans, these two monocyte populations are known for a longer time and are predominantly determined via the expression levels of the surface markers CD14 and CD16 (Ziegler-Heitbrock H. W. et al. (2000), J. Leukoc. Biol., 67: 603-6).

Embodiments of the present invention relate to methods for inhibition of monocyte invasion comprising: contacting the monocytes with an antibody which can specifically bind to the plasminogen receptor ENO1. Preferably, the contacting is carried out in vivo or in vitro. The term "in vitro" is understood in its broadest possible form in this context. It relates to any event that takes place outside of a living body, such as methods in cell culture, tissue culture or organ culture. The term "in vitro" is particularly understood to also comprise a method that relates to the treatment of blood outside the body of the subject.

The present invention further relates to methods for the treatments of multiple sclerosis, rheumatoid arthritis, Crohn's disease, ulcerative colitis, or systemic Lupus erythematosus or an immune disorder in a subject. The method comprises the step of administering an antibody that can specifically bind to the plasminogen receptor ENO1.

The present invention further relates to methods for the inhibition of invasion activity of specific monocytes in a subject. The method comprises the step of administering an antibody that can specifically bind to the plasminogen receptor ENO1.

All of the preferred implementations and variants of the invention and definitions that have already been presented above evidently also relate to the aforementioned methods in the corresponding manner.

BRIEF DESCRIPTION OF THE DRAWINGS

FIG. 1A shows that LPS induced the expression of ENO1 on cell surface, as evidenced by the increase and right-shift of fluorescent cell population in FACS scan. Data in FIG. 2B and FIG. 2C show that ENO1 is up-regulated in the CD11b$^{high}$ (FIG. 2B) and Mac3$^{high}$ (FIG. 2C) cells of inflammatory PBMC.

FIG. 7D shows the sequences of ENO1 peptide 1 (FD Q D D W G A W Q K F TA (SEQ ID NO: 40)) and peptide 2 (K R I A K A V N EK S (SEQ ID NO:41)) between amino residue number 296 and 336 of human ENO1 (SEQ ID NO:39), which participate in human ENO1 and EN10 mAb binding.

FIG. 8A shows the effect of EN10 mAb on the total peritoneum cell counts, and FIG. 8B shows no effect on neutrophil counts after administration of EN10 mAb.

FIGS. 12A and 12B. shows the generation of rat anti-mouse ENO1 antibody hybridomas and verification of each monoclonal antibody clones by the binding ELISA and the competition ELISA. The OD reading from the ELISA assays is shown next to each clone. The procedures for the generation of hybridoma, and the production of each antibody and verification of antibody by the binding ELISA and the competition ELISA were described in Example 12. The data show that 5 of 75 hybridomas antibodies may recognize the orthologous epitope of EN10 mAB in mouse ENO1 protein.

DETAILED DESCRIPTION OF THE INVENTION

Embodiments of the invention relate to methods for the treatments of various ENO1-related diseases or disorders. ENO1-related diseases or disorders may include inflammatory diseases or immune disorders. Examples of inflammatory diseases include multiple sclerosis, rheumatoid arthritis, Crohn's disease, ulcerative colitis, and systemic Lupus erythematosus. Examples of immune disorders include chronic obstructive pulmonary disease (COPD), asthma, allergy, psoriasis, type 1 diabetes mellitus, artherosclerosis and osteoporosis. The methods use an antagonist that can bind to ENO1 to inhibit its function as a receptor for plasminogen. By such inhibition, plasminogen activation is inhibited, thereby downstream reactions that involve plasmin activity is prevented or reduced. The antagonists against ENO1 may be antibodies, which may be polyclonal antibodies, monoclonal antibodies, or other modified antibodies that can bind ENO1 and inhibit ENO1's function in the activation of plasminogen.

Embodies of the invention will be further illustrated with specific examples set forth below. One skilled in the art would appreciate that these examples are for illustration only an dare not intended to be limiting because variations and modifications are possible without departing from the scope of the invention.

EXAMPLES

Example 1

To evaluate the ENO1 binding affinity of anti-human ENO1 antibody EN10 mAb, the hybridomas were grown in RPMI containing 10% fetal calf serum (FCS). After one week culture, $1\times10^6$ cells were collected, washed with PBS, resuspended in 200 ul RPMI medium, and injected into severe combined immunodeficiency (SCID) mice by IP injection. Three weeks later, acites of mice was collected and diluted to 15 ml. Antibody was further purified by 40% ammonium sulfate and Protein A column (Montage antibody purification kit Millipore) according to procedures known in the art. The purified antibody was concentrated with an Amicon Ultra-15 centrifugal filter device, following the protocols provided by the manufacturer (Millpore). The purity of antibody was analyzed by 12% SDS PAGE.

Four hundred (400) ng of human ENO1 protein was coated on a 96-well ELISA plate, and the plate was further washed with PBS. Serial dilutions from $1\times10^{-12}$ to $1\times10^{-8}$ M of EN10 mAb antibody were added to the plate, and the plate was incubated at 37° C. for 1 hour. A goat anti-mouse IgG conjugated with hypoxanthine phosphoribosyltransferase (HPRT) was added. After 1 hour, 3,3',5,5'-Tetramethylbenzidine (TMB) was added and OD405 was read. Every study was repeated three times. Data were presented as mean±SD. OD readings and concentrations of antibodies were used to make a multiple scatter plot using Sigmaplot. The $K_d$ values were predicted by four parameter logistic fit.

Figure 1:
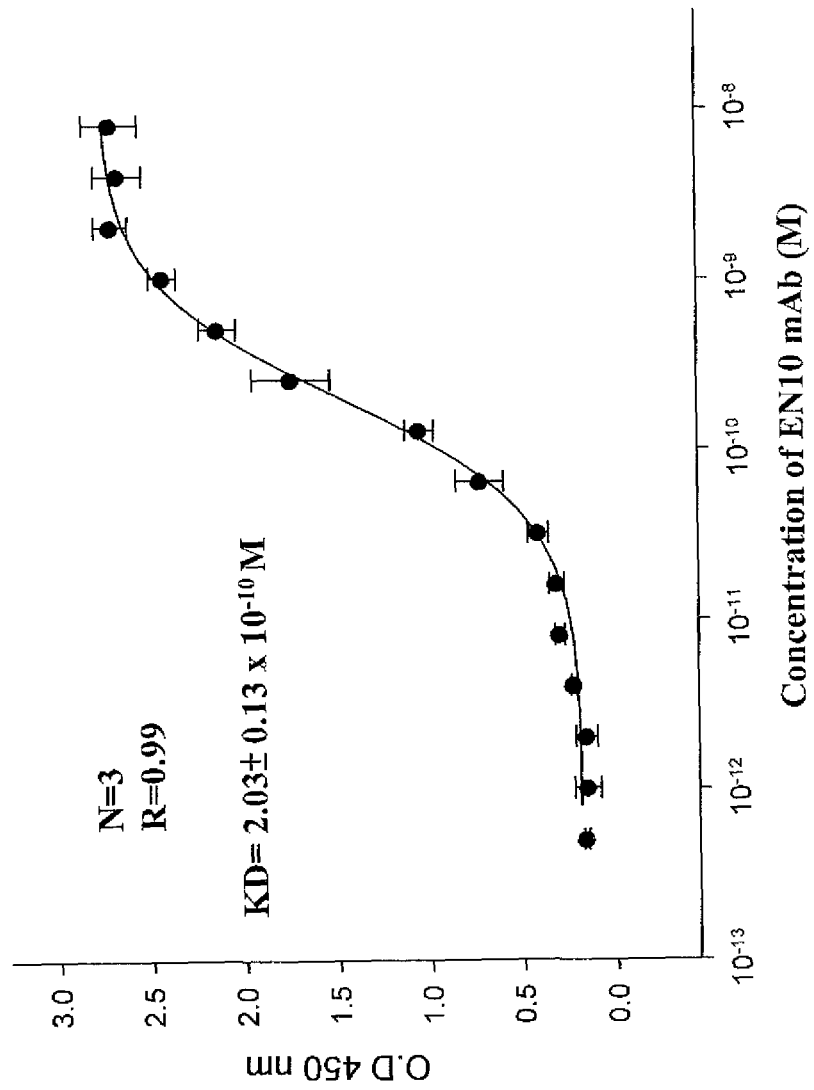
FIG. 1 shows ELISA results from ENO1 binding by a mouse anti ENO1mAb isolated from the ascites of hybridoma. Ammonium sulfate purification, protein A column purification, and SDS-PAGE purification were performed as described in Example 1. These data show the $K_d$ of anti-human ENO1 antibody EN10 mAb.

The results of this experiment are shown in FIG. 1. Antibody EN10 mAb had productivities from 20.4 mg to 4.6 mg per mice. The $K_d$ value of EN10 mAb antibody was $2.03\pm0.12\times10^{-10}$ M (N=3). This result suggests that EN10 mAb antibody can recognize the human ENO1 protein and has a favor affinity with a $K_d$ value of about $2.03\pm0.12\times10^{-10}$ M (N=3).

Example 2

It is known that ENO1 protein is up-regulated in mouse inflammatory monocytes in vivo and in vitro (Wygrecka, M. et al. (2009). Blood. 113:5588-5598). To assess the ENO1 expression level in human PBMC in the inflammatory status, fresh blood samples were collected from normal volunteers following the IRB committee codes of the Development Center for Biotechnology, Taiwan. The blood was processed to purify PBMC using Ficoll-Hypaque gradient centrifugation. The density of Ficoll-Hypaque (Pharmacia, France) was adjusted to about 1.077 g/ml. The harvested cells were grown in RPMI containing 10% fetal calf serum to a cell density of about $1\times10^6$ cells/ml. The viability of cells was checked with trypan blue stains to confirm that the overall % of lymphocytes was over 90%. PBMC was further treated with 10 mcirogram/ml of lipopolysaccharide (LPS) for 6 hours. Cells were washed with PBS two times and subjected to flow cytometric analysis. The intact cells were stained with or without EN10 mAb (1:300 dilution) and with rat anti-human CD11b or Mac3 antibody. The stained cells were visualized with FITC-conjugated goat anti-mouse IgG for the EN10 mAb and PE-conjugated anti-rat IgG for the CD11b or Mac3 antibody (Becton Dickinson). The samples were then analyzed with FACScan flow cytometer (Becton Dickinson). ENO1 and CD11b+ expression was measured by the resulting fluorescence intensity.

Figure 2A:
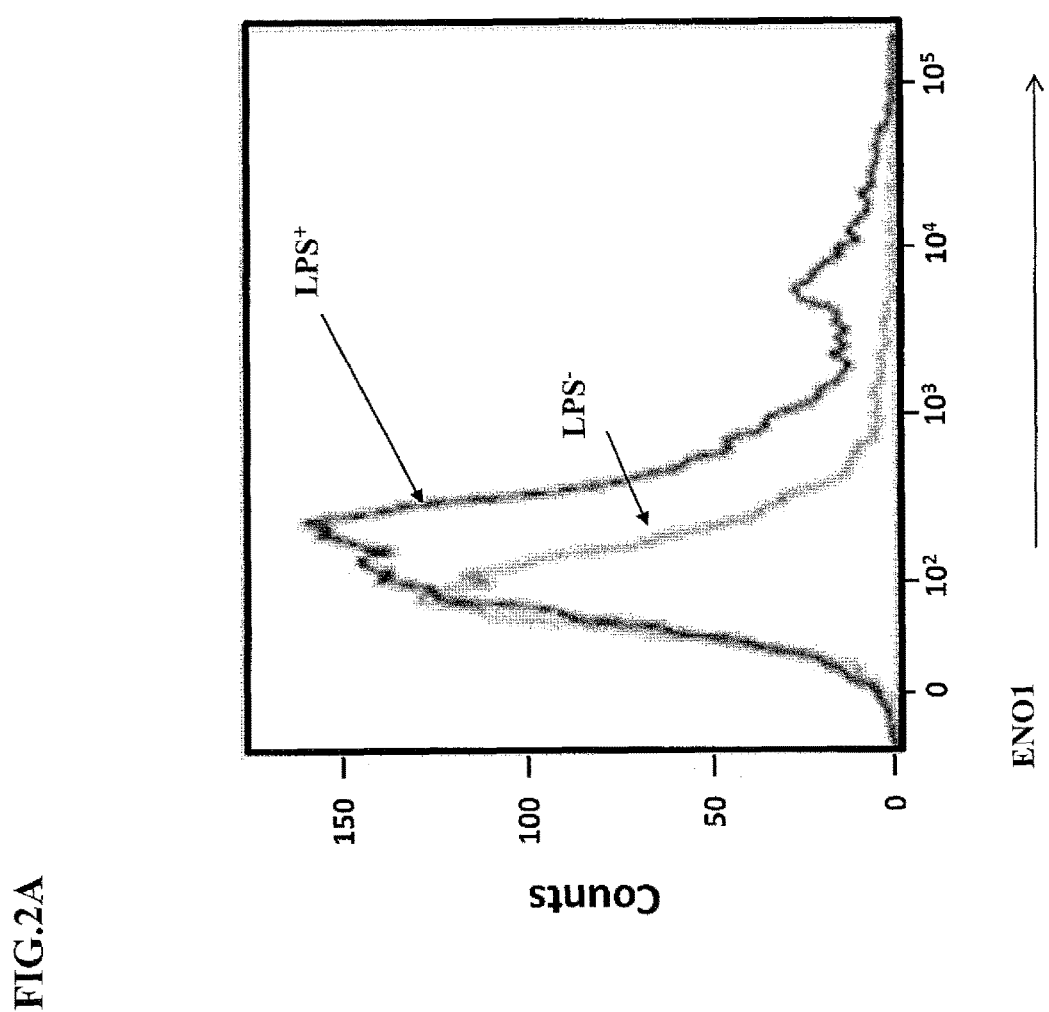
FIGS. 2A, 2B and 2C show results of ENO1 expression on the surface of CD11b+ cell when normal human PBMC is treated with LPS. The induction of ENO1 expression by LPS in normal human PBMC was performed as described in Example 2.
Figure 2B:
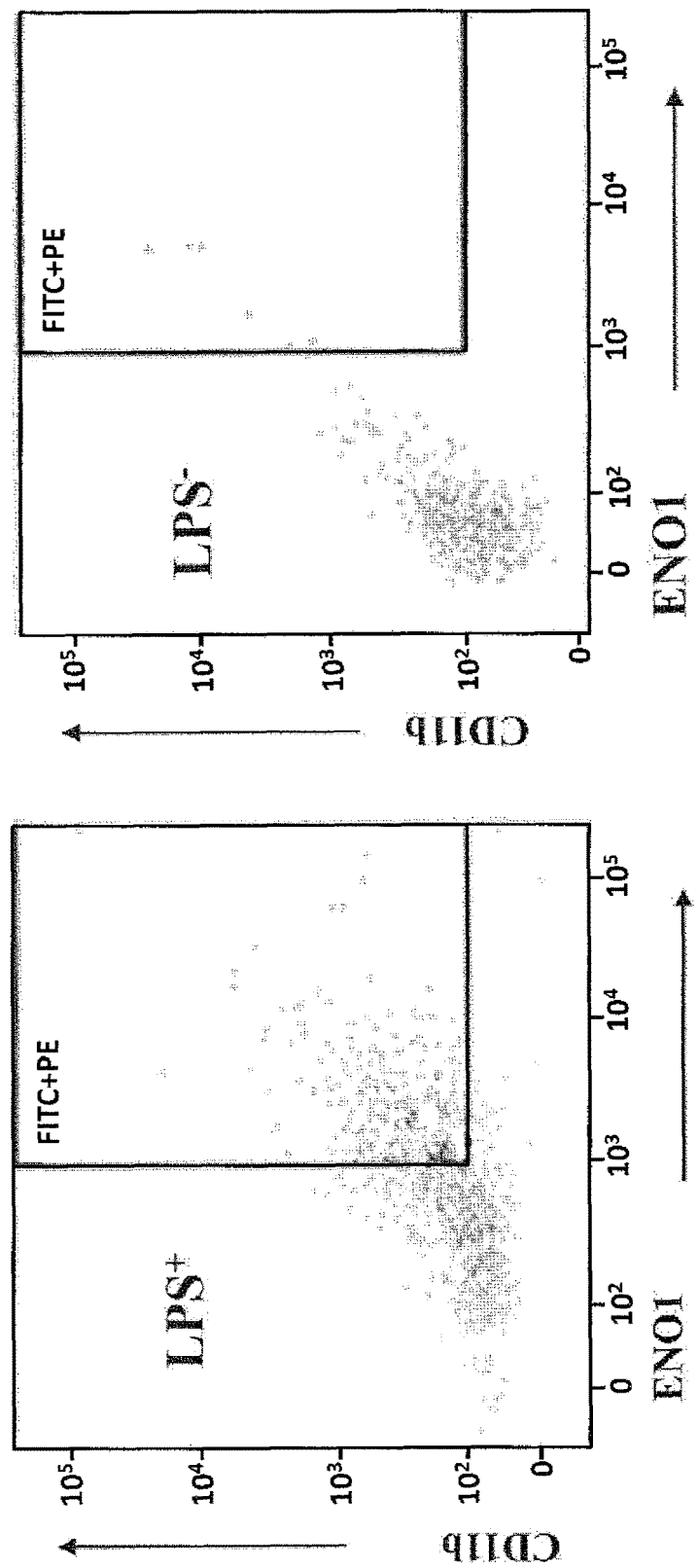
Figure 2C:
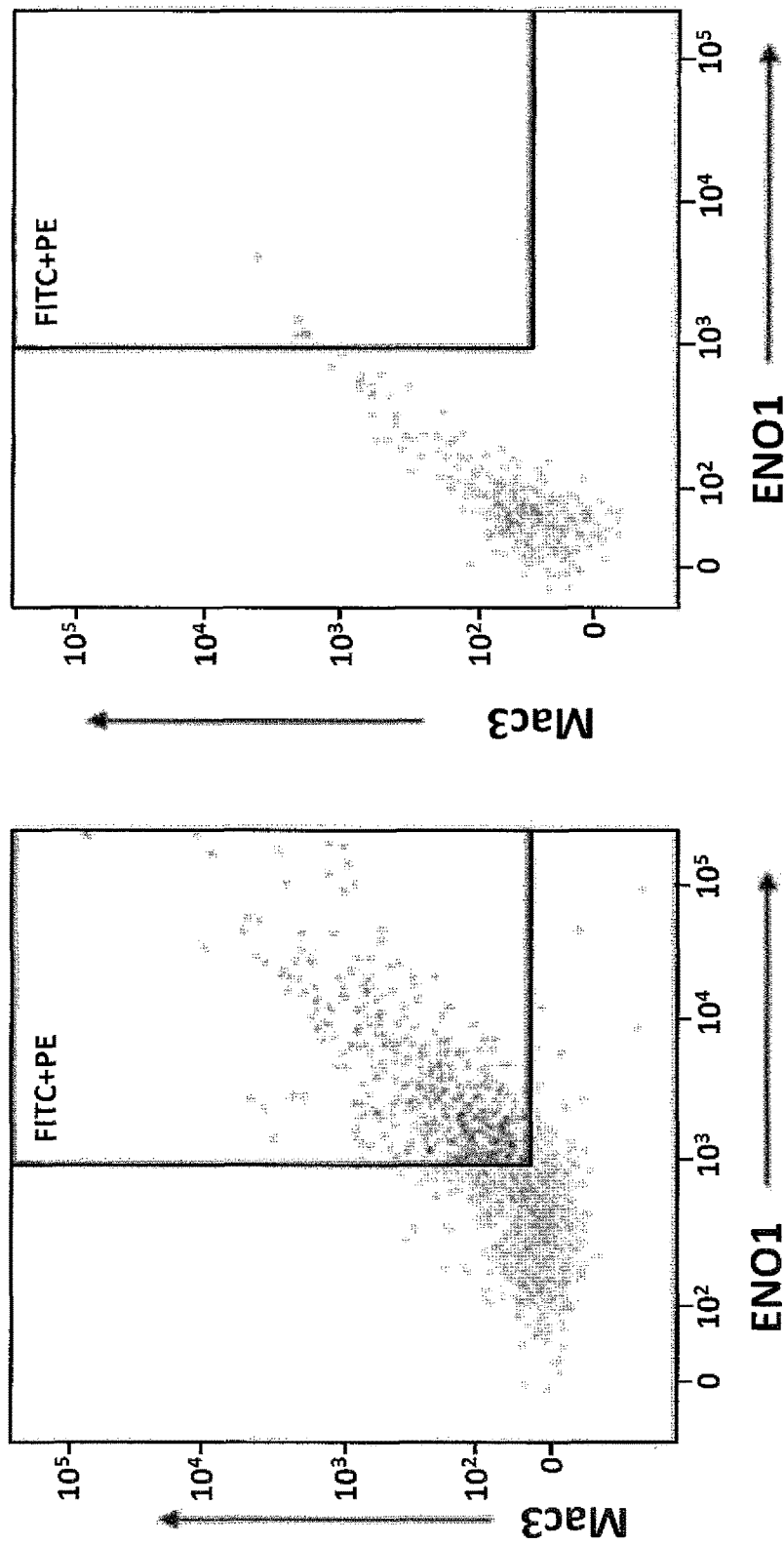

Results from these experiments are shown in FIG. 2A. Treating normal PBMC with LPS and EN10 mAb shifts the histogram to the right, as compared to incubating the cells without LPS and with EN10 mAb. This observation indicates that normal PBMC express ENO1 on their cell surface when cells are in inflammation condition (e.g., stimulated with LPS). Furthermore, cell populations with high ENO1 expression can be identified. As shown in FIG. 2B and FIG. 2C, Mac3+ and CD11b+ cell populations also increase in the LPS-treated human PBMC, as compared to cells without treatment. The high ENO1 expression cell population co-relates with the $CD11b^{high}$ and $Mac3^{high}$ cells (FIG. 2B and FIG. 2C). These results indicate that ENO1 protein is up-regulated on the surfaces of activated monocytes and macrophages.

Examples 3

Wygrecka's study indicates that ENO1 plasminogen receptor activity is very important for monocytes to transmigrate into inflammatory sites (Wygrecka, M. et al., (2009), Blood., 113:5588-5598). To assess the capability of EN10 mAb to inhibit the ENO1 plasminogen receptor activity of human monocytes, a human U937 monocyte cell line was grown in RPMI containing 10% FCS. Cells were treated with 10 microgramlml of LPS for 6 hours to induce ENO1 protein expression on the cell surface. $1.5\times10^6$ cells/ml in PBS were then pre-incubated with1 microgram/nil human Lys-plasminogen and 10 microgram/ml of EN10 mAb for one hour, respectively. Samples were washed with PBS twice and 3 nM of tissue specific plasminogen activator and 0.5 mM of chromogenic substrate S-2251 were added. After one hour incubation at 37° C., OD 405 was read. Every study was repeated three times, and the antagonist activity was analyzed. Data were presented as mean SD. T-test was used to compare each group. P values <0.05 were considered statistically significant.

Figure 3:
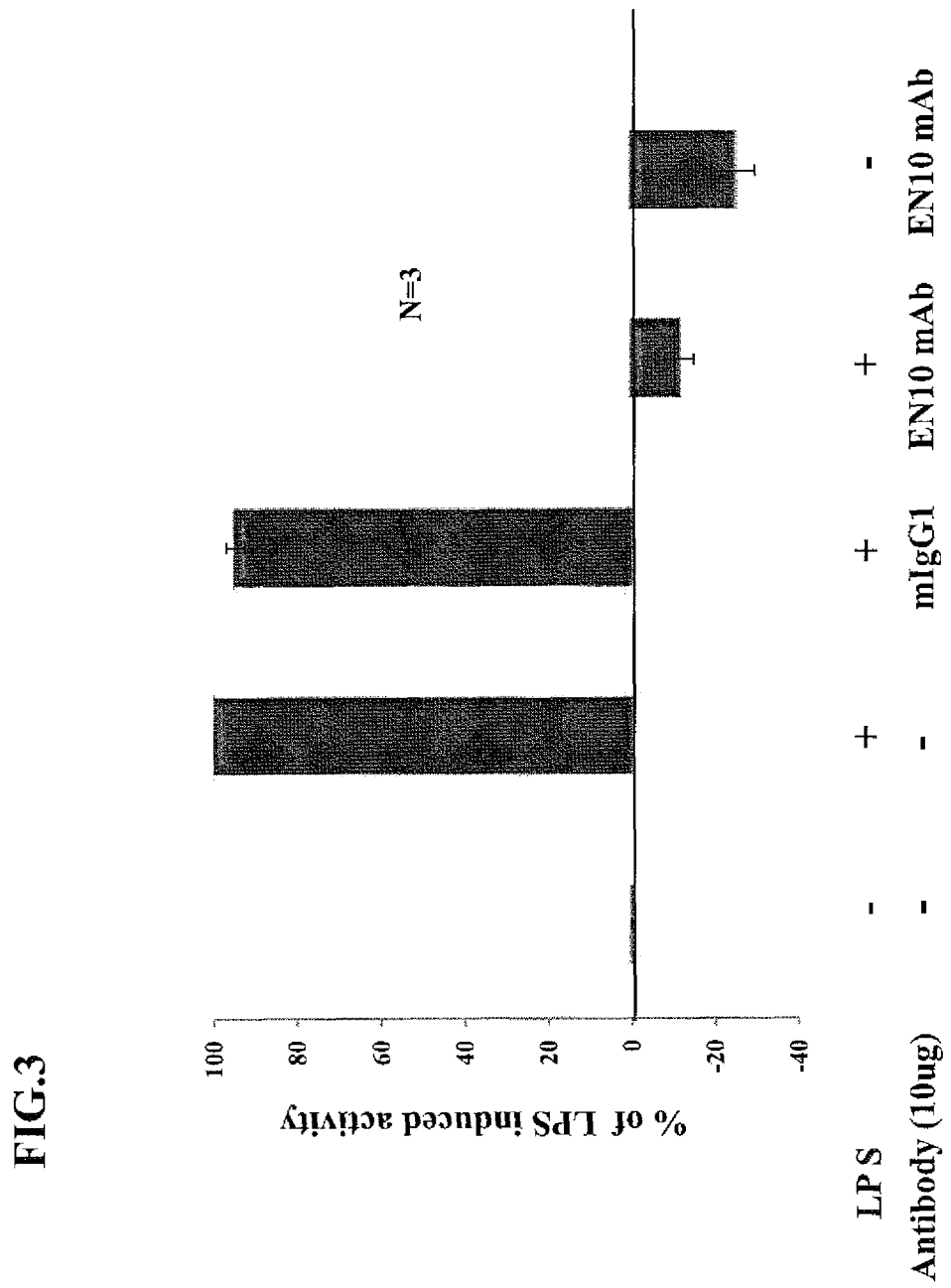
FIG. 3 shows the results of effects on LPS-induced U937 fibrinolytic activity by EN10 mAb (anti-ENO1 antibody) isolated from acites of hybridomas. The induction of ENO1 expression by LPS on human U937 monocytic cell line and plasmin activity assay were performed as described in Example 3. These data show that EN10 mAb can inhibit ENO1 plasminogen receptor function on monocytes.

Results of this experiment are shown in FIG. 3. EN10 mAb had a high ENO1 plasminogen receptor antagonist activity and can achieve 100% inhibition of LPS-induced specific ENO1 activity. Therefore, EN10 mAb would have a good potential in inhibiting the transmigration of monocytes to the target organs.

Examples 4

The result of Example 3 suggests that EN10 mAb can inhibit the ENO1 plasminogen receptor activity and results in the inhibition of plasminogen activation and transmigration activity in the LPS-stimulated human monocytes. This result is further supported by other literature reports indicating that monocytes of plasminogen-null mice lose the migration capability and infiltration activity in a mouse non-infectious inflammation model (Ploplis, V. A. et al., (1998) Blood, 91:2005-2009).

To assess whether compromising the ENO1 plasminogen receptor activity results in the alleviation of invasion activity of activated monocytes, a human monocyte U937 cell line was grown in RPMI containing 10% FCS. Cells were treated with 10 microgram/ml of LPS for 6 hours to induce ENO1 protein expression on cell surface. After being mixed with 5 to 50 microgram/ml of EN10 mAb, $2 \times 10^4$ cells were seeded in the top chamber of a two-chamber assay system containing 15 micro molar of Lys-plasminogen and incubated for 24 hours with media containing 10% FBS and 10 nM MCP-1 in the lower chamber. An anti-mouse IgG was used as a negative control group. Two chambers were separated by a micropore filter (8 micrometer pore size) coated with matrigel. After the incubation period, cells in the lower chamber were counted by a hemocytometer under a microscope. Every study was repeated three times. Data are presented as mean±SD. The T-test was used to compare each groups. P values <0.05 were considered statistically significant.

Figure 4:
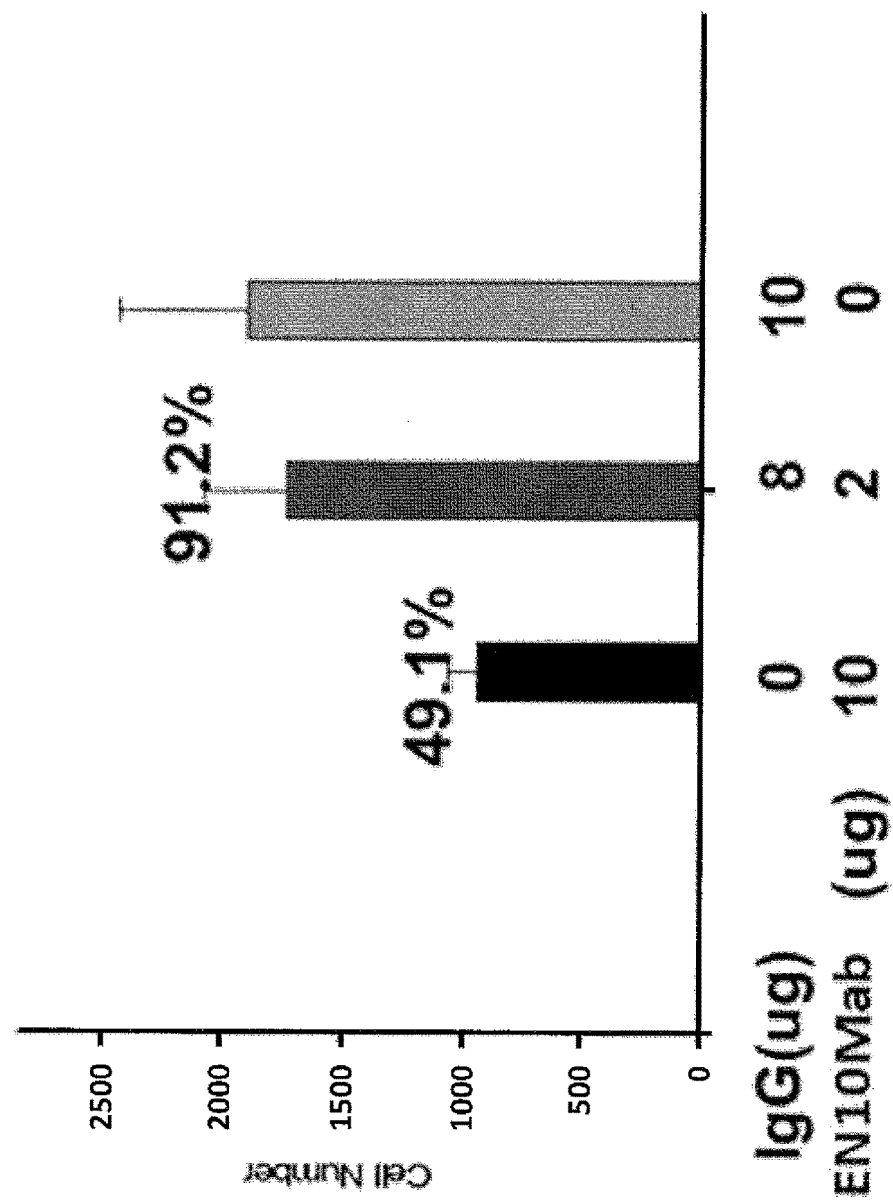
FIG. 4 shows results of invasion activities of human U937 monocytic cell line treated with different concentrations of EN10 mAb when the surface ENO1 expression of cells is induced by LPS. The detailed procedures were performed as described in Example 4. These data show that the EN10 mAb inhibits the invasion activity of U937 cells in a dose-dependent manner.

The results are shown in FIG. 4. When LPS-treated U937 cells were treated with 5 to 50 microgram/ml of EN10 mAb, the invasion activity of U937 was from 90.2±2% to 49.1±1% (N=3) of the control IgG. These results indicate that EN10 mAb can alleviate the invasion capability of activated U937 monocytes by compromising the ENO1 plasminogen receptor activity in a dose-dependent manner. By targeting ENO1 protein on the surface of inflammatory monocytes, it is feasible to inhibit cells entering affected sites using EN10 mAb.

Examples 5

To know the expression level of cell surface ENO1 after inflammatory stimulation, human U937 monocytes were grown in RPMI containing 10% FCS. Cells were treated with 10 microgram/ml of LPS for 6 hours to induce ENO1 protein expression on the cell surface. For flow cytometric analysis, the intact whole cells were stained with or without EN10 mAb (1:300 dilution), visualized with FITC-conjugated goat antiserum (Jackson Lab), and analyzed with FACScan flow cytometer (Becton Dickinson). ENO1 expression was measured by the resulting fluorescence intensity.

Figure 5:
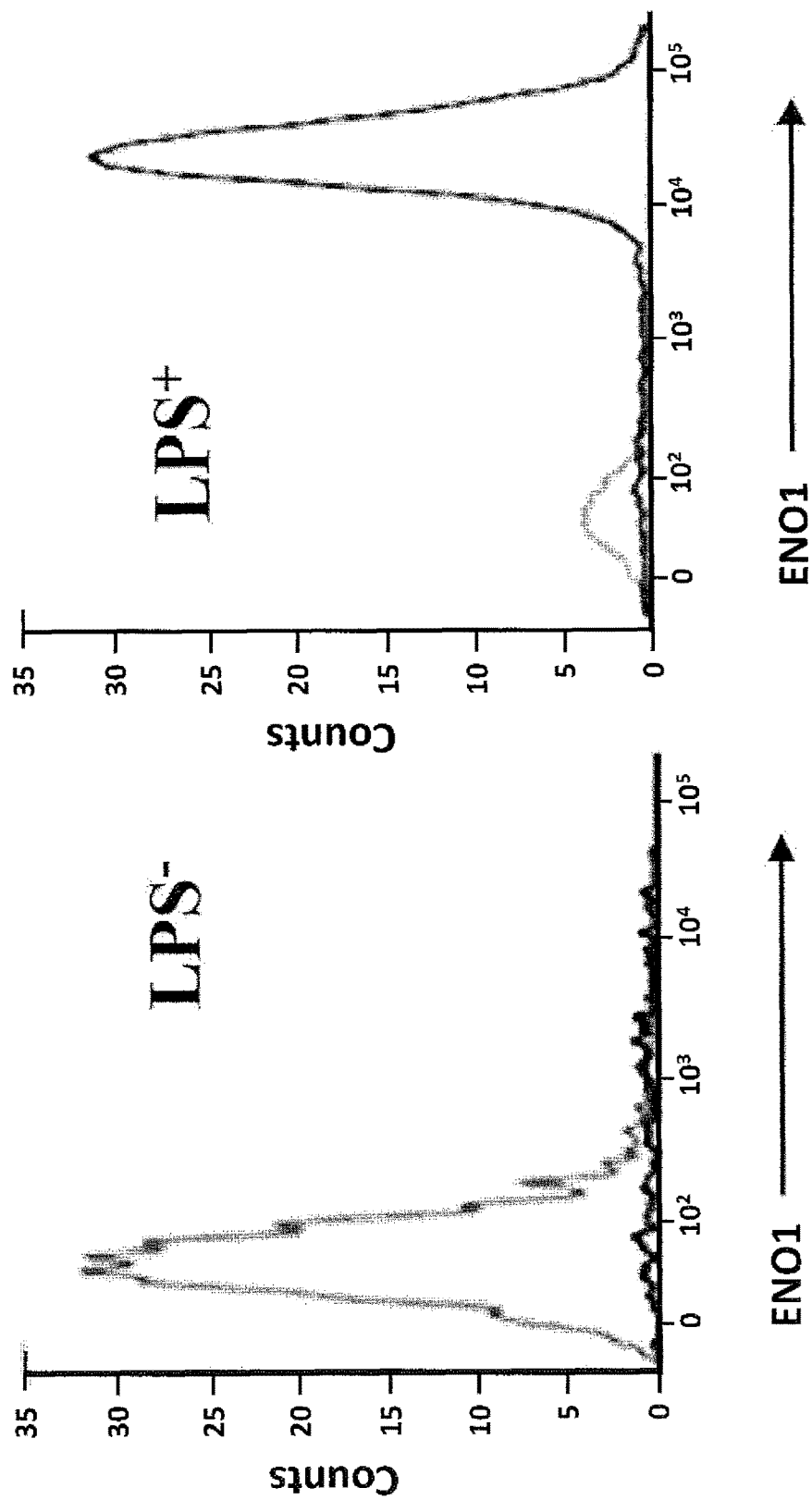
FIG. 5 shows that the EN10 mAb recognizes the cell surface ENO1 on the human U937 monocytes treated with LPS. The detailed procedures were performed as described in Example 5.

Results from these experiments are shown in FIG. 5. Incubating U937 with LPS and EN10 mAb shifts the histogram to the right, as compared to incubating the cells without LPS but with EN10 mAb. This result indicates that U937 cells express ENO1 on their cell surfaces when they are stimulated by LPS. These data support the notion that EN10 mAb recognizes LSP-induced surface ENO1 on the monocytes.

Example 6

Epitope Mapping

Antibody Epitope Mapping

To determine the epitope of EN10 mAb on the human ENO1 protein, two forward primers, with the nucleotide sequences of 5'-GGATCCGCAGCAAACTTCA-GGGAAGCCATG-3' (SEQ ID NO:1), and 5'-GGATCCTC-GAAGATCCCTTTGACCAGGATG-3' (SEQ ID NO:2), and a reverse primer 5'-TCAGGCTGAAAATCTCTCATC-CGC-3' (SEQ ID NO:3) were designed. An E. coli expression plasmid pTRC-HIS ENO1 containing the human ENO1 cDNA gene was used as a template to amplify ENO1 deletion mutants. Primers with SEQ NO:1 and SEQ NO:2 were used as forward primers, with the SEQ ID NO:3 as a reverse primer, to amplify deletion mutants Δ1-189 (FIG. 6A) and Δ1-297 (FIG. 6A), respectively. The other set of primers, having the sequences of 5'-GGATCCTATCTAT-TCTCAAGATCCATGCC-3' (SEQ ID NO:4) and 5'-CTC-GAGGTCATGGTGTCTCATCGTTCGCTCGAG-3' (SEQ ID NO:5), was used to amplify a deletion Δ297-434 (in FIG. 6A) mutant. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of the forward primer, and 1 microL of the reverse primer was prepared in a final volume of 50 microL with double distilled water and subjected to PCR. A cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1-TOPO vector (manufactured by Invitrogen) for subcloning in accordance with the attached instruction manual. M13 forward 5=-GTAAACAAC-GACGGCGAG-3' (SEQ ID NO: 6) and M13 reverse 5'-CAG GAAACA GCT ATG AC-3' (SEQ ID NO: 7) primers were then used to determine the nucleotide sequence. Every mutation clone with the correct sequences was digested with restriction enzymes BamHI and XhoI, and the digestion products were subjected to 2% agarose gel electrophoresis. The insertion fragment of each mutant was cut from the agarose gel and purified with a Gene Clean Kit in accordance with the attached instruction manual provided by the manufacturer (BIO101). The BamHI and XhoI DNA fragment of each mutant was ligated to the BamHI and XhoI sites of an E. coli expression vector pTRC His A (Invitrogen). The resulting plasmid was transformed into E. coli BL21 Rosseta. The ENO1 mutation protein was expressed in E. coli by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of each human ENO1 mutant protein was coated on a 96-well ELISA plate and the plate was washed by PBS. 10 microgram of EN10 mAb was added to the plate and the plate was incubated at 37° C. for 1 hours. After the binding complex was washed with PBS twice, a goat anti-mouse IgG conjugated with HPRT was added, After 1 hours incubation, TMB was added. The binding affinity was determined by the readings of OD 405. Each study was repeated three times. Data are presented as mean±SD. The T-test was used to compare activity between each group. P values <0.05 were considered statistically significant.

Figure 6A:
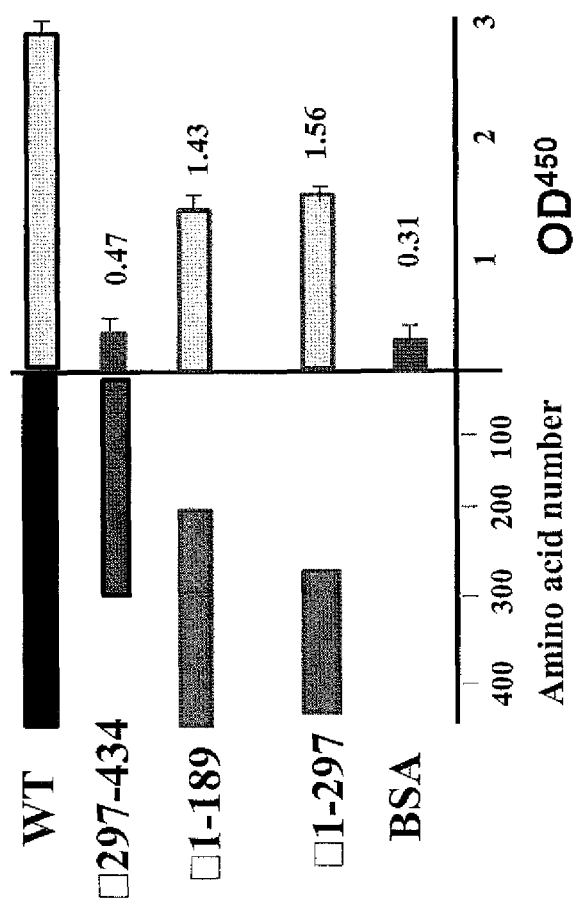
FIG. 6A shows the EN10 mAb binding activities of deletion mutants of ENO1. The binding epitope of EN10 mAb is located between the amino residue number 297 and 434 of human ENO1 protein because deletion of this fragment essentially abolishes antibody binding. The large portion deletion of ENO1 to determine the binding region of EN10 mAb was performed as described in Example 6.

The results are shown in FIG. 6A. ENO1 mutants Δ1-189 and Δ1-297 have OD405 readings about 1.43±0.18 and 1.56±0.08 (N=3) (in FIG. 6A), which are about 42% and 39% of that of the wild type ENO1 (2.87±0.08) (N=3), respectively. However, when amino acid residues from 297 to 434 were deleted, the binding activity of this mutated ENO1 to EN10 mAb was lost, as compared with the BSA background. These results suggest that amino acid residues from 297 to 434 are required for ENO1 protein binding to EN10 mAb and the decrease in the binding activity of mutants Δ1-182 and Δ1-297 may be due to the instability or conformation change of the mutant proteins.

To further explore the epitope of EN10 mAb in the ENO1 protein, 5 reverse primers, having sequences of 5'-CTCGA-GAGGGATCTTCGATAGACACCACTGGG -3' (SEQ ID NO:8), 5'-CTCGAGCTACCTGGATTCCTGCACTG-GCTG-3' (SEQ ID NO:9), 5'-CTCGAGACTTCTCGT-TCACGGCCTTGGCGATC-3' (SEQ ID NO:10), 5'-CTC-GAGACTTCTCGTTCACGGCCTTGGCGATCC-3' (SEQ ID NO:11), 5'-CTCGAGCAGTCTCCCCCGAACGAT-GAGACACC-3' (SEQ ID NO:12), and 5'-CTCGAG CAC-CAGTCTTGATCTGCCCAGTGCAC-3' (SEQ ID NO:13) were designed. An E. coli expression plasmid pTRC-HIS ENO1 containing the human ENO1 cDNA gene was used as a template to amplify the ENO1 deletion mutants. SEQ ID NO:4 were used as the forward primer to amplify deletion mutants 296-434, 316-434, 336-434, 376-434 and 396-434 with the SEQ ID NO:8, SEQ ID:9, SEQ ID:10, SEQ ID:11, SEQ 1D:12, and SEQ ID:13 primers, respectively. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of forward primer, and 1 microL of reverse primer was prepared in a final volume of 50 microL with double distilled water and subjected to PCR. A cycle of 94 degree C. for 10 minutes was used. Then, a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1-TOPO vector (manufactured by Invitrogen) for subcloning in accordance with the attached instruction manual. M13 forward (5'-GTAAACAACGACGGCGAG-3' (SEQ ID NO:6) and Ml3 reverse (5'-CAGGAA ACAGC-TATGAC-3' (SEQ ID NO:7) primers were then used to determine the nucleotide sequence. Every mutation clone with the correct sequence was digested with restriction enzymes BamHI and XhoI and the digestion product was subjected to 2% agarose gel electrophoresis. The DNA fragment of each mutant was isolated from the agarose gel and purified with a Gene Clean Kit in accordance with the attached instruction manual provided by the manufacturer (BIO101). The BamHI and XhoI DNA fragment of each mutant was ligated into the BamHI and XhoI sites of an E. coli expression vector pTRC His A (Invitrogen). The resulting plasmid was transformed into E. coli BL21 Rosseta. The ENO1 mutation protein was expressed in E. coli by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of human ENO1 protein or mutant protein was coated on a 96-well ELISA plate and the plate was washed by PBS. 10 microgram of EN10 mAb was added and incubated at 37° C. for 1 hour. After the binding complex was washed with PBS twice, a goat anti-mouse IgG conjugated with HPRT was added. After 1 hour incubation, TMB was added. The binding affinity was determined by the readings of OD 405. Each study was repeated three times. Data are presented as mean±SD. The T-test was used to compare activity between each group. P values <0.05 are considered statistically significant.

Figure 6B:
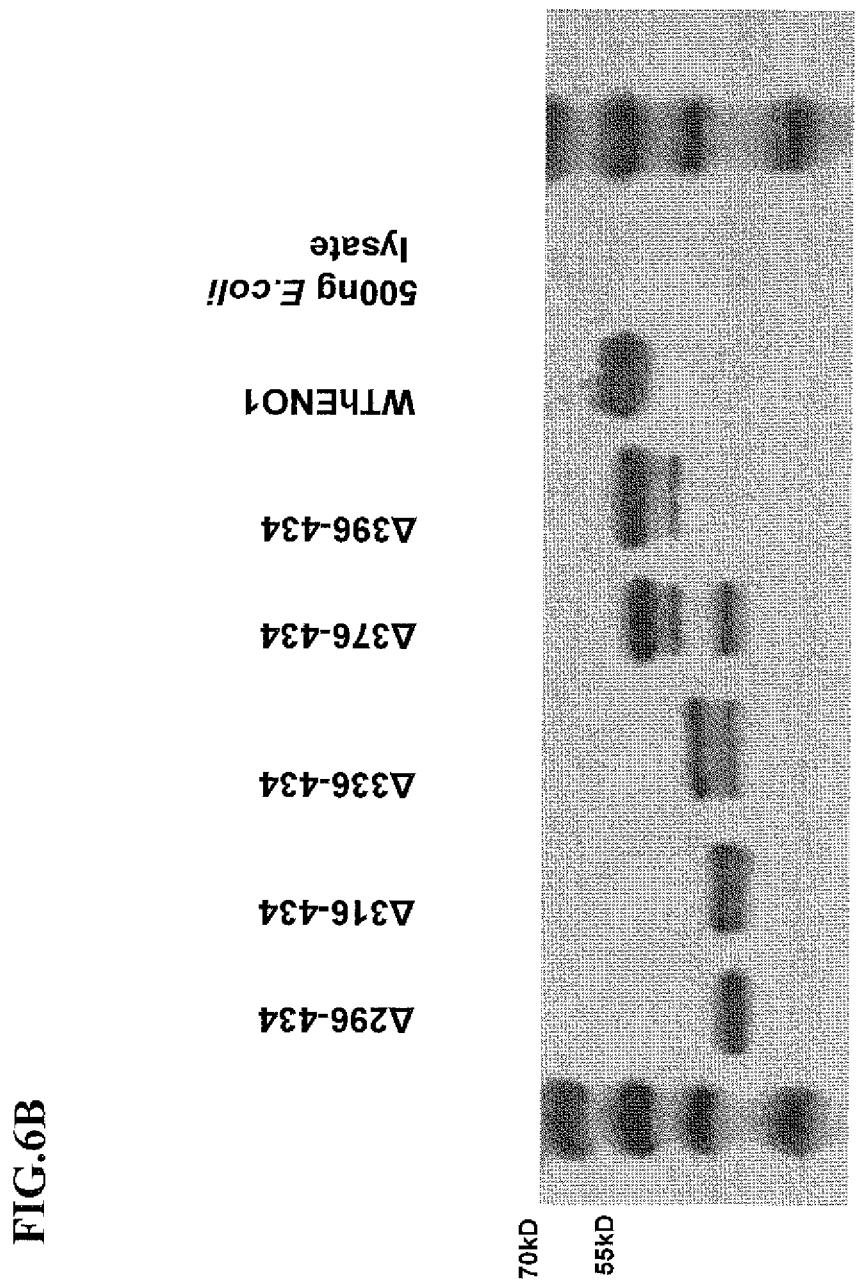
FIG. 6B shows the 12% SDS PAGE of 6 C-terminal deletion mutant protein of ENO1 purified from *E. coli*. The detailed procedures for the purification of ENO1 deletion mutants are described in Example 6.
Figure 6C:
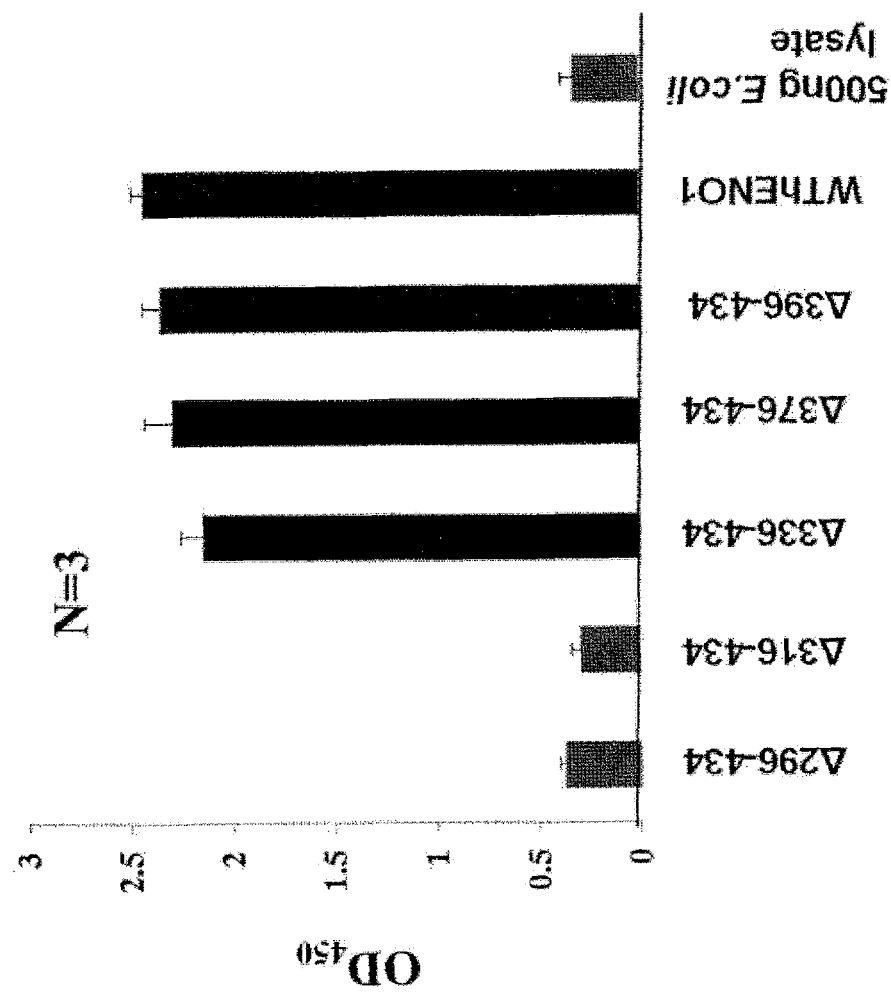
FIG. 6C shows the EN10 mAb binding activities of 6 C-terminal deletion mutants of ENO1. The binding epitope of EN10 mAb is located between amino residue number 296 and 336 of human ENO1 protein. The large portion deletion of ENO1 to determine the binding region of EN10 mAb was performed as described in Example 6.

The 12% of SDS PAGE of each mutant and the wild type protein are shown in the FIG. 6B. The molecular weight of each mutant increases from the mutant 296-343 to the wild type. This result suggests that we can yield the whole protein from each mutant even though some degradation of mutants 336-434 and 376-434 can be seen. As showed in the FIG. 6C, there is no significant difference between the EN 10 mAb binding affinity of the wild type ENO1 and those of deletion mutants 336-434, 376-434, and 369-343. However, when amino acid residues from 296 to 316 and 317 to 336 are deleted, the EN10 mAb binding activities of these two ENO1 mutants are lost, as compared with that the E. coli cell lysate background. These results suggest that amino acid residues in the region from around 296 to around 336 ($^{296}$FDQDDWGAWQKFTASAGIQVVGDDLTVTNPKRI-AKAVNEKS$^{336}$, SEQ ID NO:39) are important for the ENO1 protein binding with EN10 mAb.

Example 7

Alanine Scanning

To further explore which residues from 296 to 336 of human ENO1 are important for EN10 mAb binding, the crystal structure of ENO1 was downloaded from protein data bank (pdb-entry: 2PSN). After the structure analysis, amino acid residues D300, W301, G302, Q305, K306, A309, K326, K330, N333, E334, and K335 are predicted to be exposed on the protein surface and are candidates for mutations to analyze whether they are indeed important for EN10 mAb binding. 10 of these 11 residues were chosen to be mutated to alanine, except for A309 which was mutated to glycine using the QuickChange II site-directed mutagenesis Kit in accordance with the attached instruction manual provided by the manufacturer (Agilent Technology). The following mutagenic oligonucleotides for alanine scanning (Table 1) were generated by Genomics BioScience and Technology Co., Ltd.

TABLE 1

Oligo Sequences

5'-GATCCCTTTGACCAGGATGCCTGGGGAGCTTGGCAG-3' (SEQ ID NO: 14)

5'-CTGCCAAGCTCCCCAGGCATCCTGGTCAAAGGGATC-3' (SEQ ID NO: 15)

5'-CCCTTTGACCAGGATGACGCGGGAGCTTGGCAGAAG-3' (SEQ ID NO: 16)

5'-CTTCTGCCAAGCTCCCGCGTCATCCTGGTCAAAGGG-3' (SEQ ID NO: 17 )

5'-CTTTGACCAGGATGACTGGGCAGCTTGGCAGAAGTTC-3' (SEQ ID NO: 18)

5'-GAACTTCTGCCAAGCTGCCCAGTCATCCTGGTCAAAG-3' (SEQ ID NO: 19)

5'-GACTGGGGAGCTTGGGCGAAGTTCACAGCCAGTGCA-3' (SEQ ID NO: 20)

5'-TGCACTGGCTGTGAACTTCGCCCAAGCTCCCCAGTC-3' (SEQ ID NO: 21)

5'-GGGGAGCTTGGCAGGCGTTCACAGCCAGTGCAGG-3' (SEQ ID NO: 22)

5'-CCTGCACTGGCTGTGAACGCCTGCCAAGCTCCCC-3' (SEQ ID NO: 23)

5'-GGCAGAAGTTCACAGGCAGTGCAGGAATCCAGGTAG-3' (SEQ ID NO: 24)

5'-CTACCTGGATTCCTGCACTGCCTGTGAACTTCTGCC-3' (SEQ ID NO: 25)

5'-TCACAGTGACCAACCCAGCGAGGATCGCCAAGGCC-3' (SEQ ID NO: 26)

5'-GCCTTGGCGATCCTCGCTGGGTTGGTCACTGTGAG-3' (SEQ ID NO: 27)

5'-CAACCCAAAGAGGATCGCCGCGGCCGTGAACGAGAAG-3' (SEQ ID O: 28)

5'-CTTCTCGTTCACGGCCGCGGCGATCCTCTTTGGGTTG-3' (SEQ ID NO: 29)

5'-GAGGATCGCCAAGGCCGTGGCCGAGAAGTCCTGCAAC-3' (SEQ ID O: 30)

5'-GTTGCAGGACTTCTCGGCCACGGCCTTGGCGATCCTC-3' (SEQ ID NO: 31)

5'-GATCGCCAAGGCCGTGAACGCGAAGTCCTGCAACTG-3' C(SEQ ID NO: 32)

5'-GCAGTTGCAGGACTTCGCGTTCACGGCCTTGGCGATC-3' (SEQ ID NO: 33)

5'-GCCAAGGCCGTGAACGAGGCGTCCTGCAACTGCCTC-3' (SEQ ID NO: 34)

5'-GAGGCAGTTGCAGGACGCCTCGTTCACGGCCTTGGC-3' (SEQ ID NO: 35)

5'-CAAGGCCGTGAACGCGGCGTCCTGCAACTGCCTCCTG-3' (SEQ ID NO: 36)

5'-CAGGAGGCAGTTGCAGGACGCCGCGTTCACGGCCTTG-3' (SEQ ID NO: 37)

For amplification of each mutant, a reaction solution having a composition of 3 microL of template DNA about 30 ng, 5 microL of 10× reaction buffer, 1 microL of 10 mM dNTP mix, 1 microL of 2.5 unit pfu polymerase, 12.5 microL of 125 ng forward primer, and 12.5 microL of 125 ng reverse primer was prepared in a final volume of 50 microL with double distilled water and subjected to PCR. A cycle of 95 degree C. for 10 minutes was used. Then, a cycle of 95 degree C. for 30 seconds, 55 degree C. for 30 seconds, and 68 degree C. for 6 minute was repeated 16 times. After the PCR reaction, 1 microL of DpnI was added to each PCR tubes, incubated at 37C for 1 hour and then DpnI was heated to be inactivated at 80° C. for 20 minutes. The reaction products were transformed to 50 microL XL1-Blue competent cells in accordance with the attached instruction manual (manufactured by Invitrogen). An ENO1 R400-420 primer (5'-GCAAGGGGCACCAGTCTTGATCTG-3' (SEQ ID NO:38)) was used to determine the nucleotide sequence. Every mutation clone plasmids with correct sequences were transformed to E. coli BL21 Rosseta. The ENO1 mutation protein was expressed in E. coli by IPTG induction and purified by Ni-agarose in accordance with the attached instruction manual provided by the manufacturer (Qiagen) after the bacteria pellet was sonicated. The purity of each mutant protein was analyzed by 12% SDS PAGE.

To determine the binding activity of each mutant protein, 400 ng/100 microL of human ENO1 protein or mutated ENO1 protein was coated on a 96-well ELISA plate overnight at 4° C. and the plate was washed with PBS. The plate was blocked with 1% BSA (w/v) in PBS at room temperature for 1 hour, then washed again with 1× PBS. A primary antibody (EN10 mAb) was 2-fold serial diluted to 15 different concentrations and added to the plate at 37° C. for 1 hour. After the reaction was complete, the plate was washed 3 times with 1× PBS. A 1/8000 dilution of goat anti-mouse-HRP antibody was added and incubated at 37° C. for 1 hour, then the plate washed 3 times with 1× PBS. Then, TMB substrate was added and the reaction was allowed to proceed at room temperature for 30 minutes. The reaction was stopped by adding 1N HCl and OD 450 was read to determine the activity. Each study was repeated three times. Data are presented as mean±SD. OD readings and concentrations of antibody were used to make a multiple scatter plot using Sigmaplot™. The $K_d$ values were predicted by four parameter logistic fit.

According to the ENO1 large portion deletion study results shown in Example 6, a peptide sequence $^{296}$FDQD- DWGAWQKFTASAGIQVVGDDLTVTNPKRI-AKAVNEKS[336] (SEQ ID NO:39) from the residue number 296 to 336 is required for tight binding of ENO1 protein with EN10 mAb. "Tight binding" as used herein refers to binding between a specific binding agent (e.g., an antibody, an scFv or Fab fragment) and a ligand/target (e.g., a peptide, protein, or cell) with a dissociation constant ($K_d$) of 10 nM or lower, preferably 1.0 nM or lower.

Figure 7A:
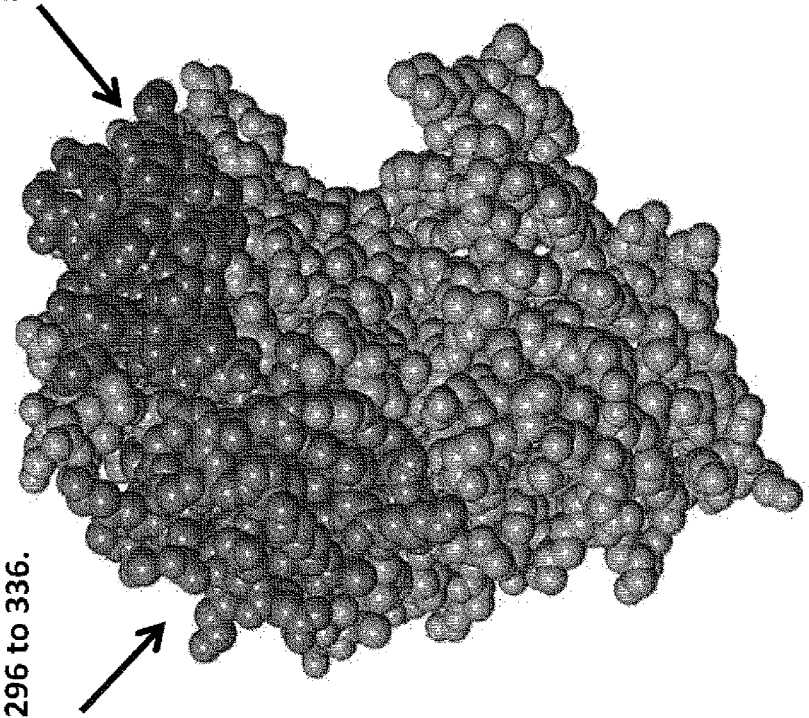
FIG. 7A depicts the crystal structure and surface-expose amino acid residues between amino number 296 and 336 of human ENO1. The structure prediction was described in Example 7.
Figure 7B:
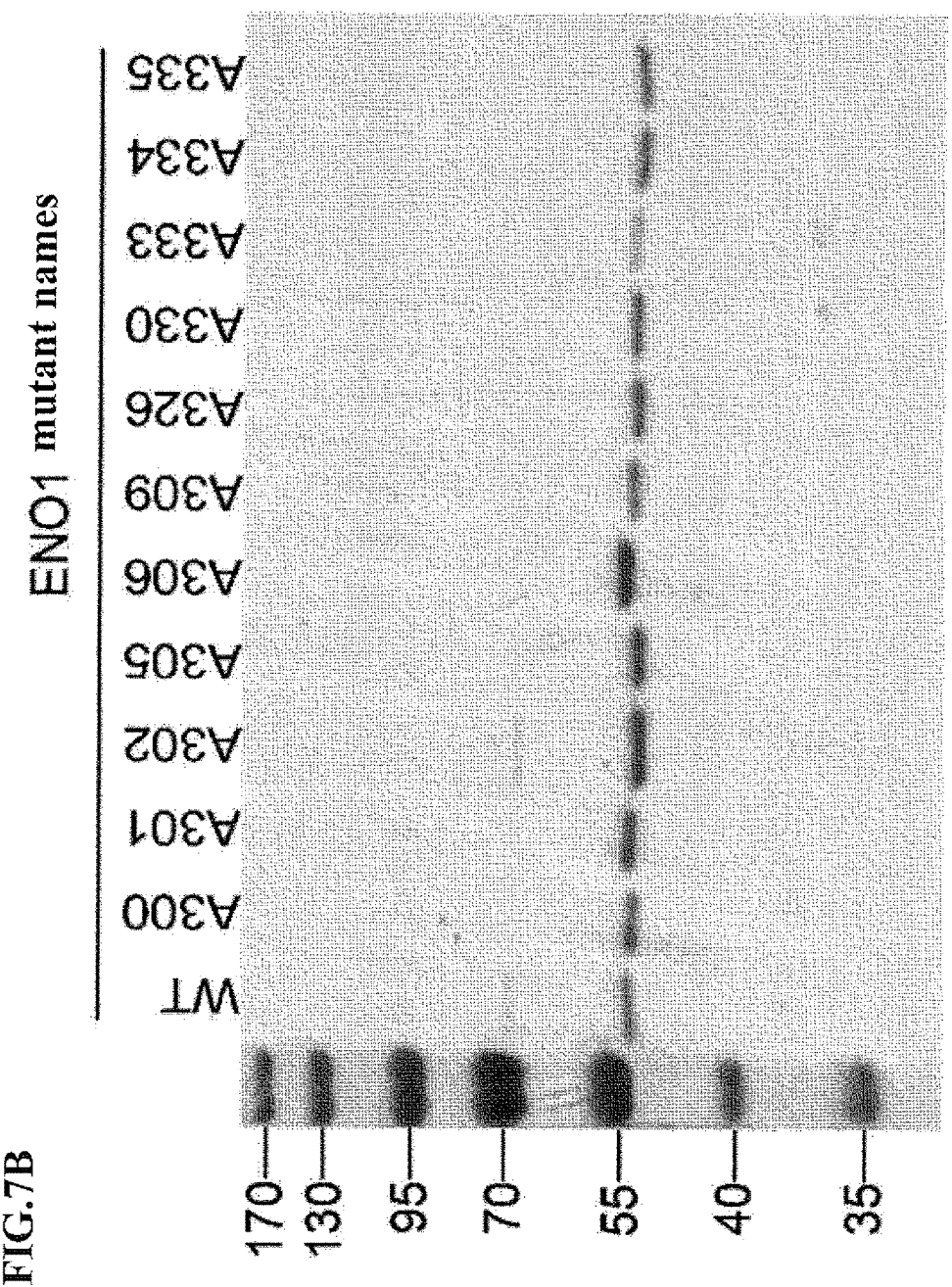
FIG. 7B shows the 12% SDS PAGE of 11 alanine scanning mutant proteins of ENO1 purified in *E. coli*. The detailed procedures for the purification of ENO1 mutation proteins are described in Example 7.

The above deletion experiments identify residues 296 to 336 on ENO1 as the region for the antibody binding. To further characterize the actual binding sites (e.g., eptitopes), the crystal structure of ENO1 was downloaded from protein data bank (pdb-entry: 2PSN) to analyze residue positions from this region. There are eleven amino acid residues including D300, W301, G302, Q305, K306, A309, K326, K330, N333, E334, and K335 exposed on the protein surface (FIG. 6A, putative epitope). By site-direct mutagenesis, these 11 amino acids were mutated and resulting mutant proteins were expressed in *E. coli* and purified, respectively (FIG. 7B). Every purified ENO1 mutant protein was analyzed for any $K_d$ changes (as compared with END 1 binding) using ELISA.

Figure 7C:
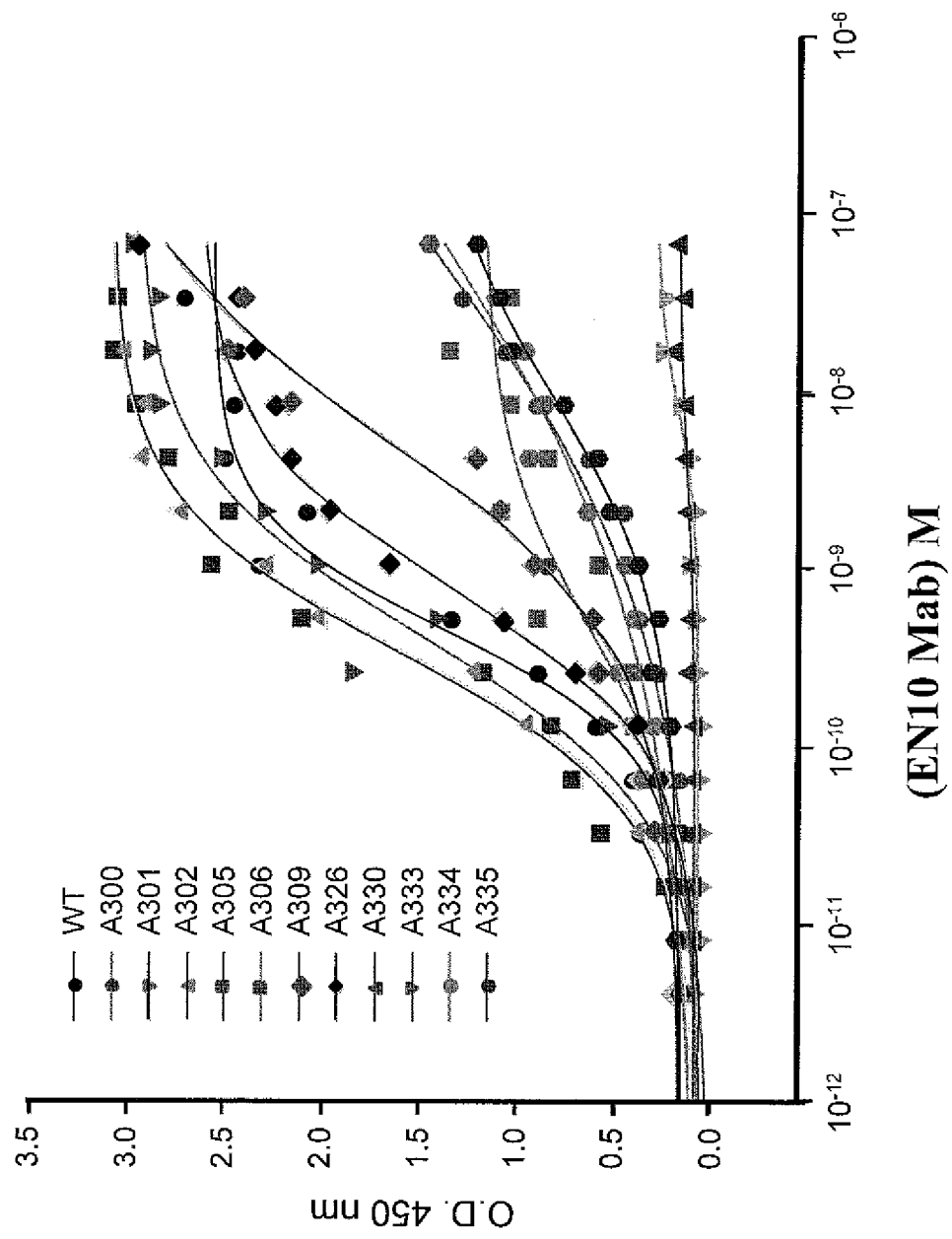
FIG. 7C shows the ENO1 binding ELISA and Kd values of 11 alanine scanning mutants against EN10 mAb. The result suggests that sequences of ENO1 peptide 1, F D Q D D W G A W Q K F TA (SEQ ID NO: 40), and peptide 2, K R I A K A V N EK S (SEQ ID NO:41), located between amino residue number 296 and 336 of human ENO1 are involved in EN10 mAb binding. The alanine scanning was performed as described in Example 7.

The results indicate that there are three functional classes of amino acid residues in these mutants. Amino acid residues W301 and K330 are important for the binding between ENO1 protein and EN10 mAb. If these two amino acid residue are mutated to alanine, respectively, the binding activities of these two ENO1 mutants to EN10 mAb are significantly abolished. The second class of amino acid residues includes A309, E334, K335 and D300. If E334, K335 and D300 are mutated to alanine or the A309 is mutated to glycine, respectively, the binding activities of these ENO1 mutants to EN10 mAb are compromised. The rest of amino acid residues including G302, Q305, K306, N333, and K326 belong to the group of amino acids residues that have no significant binding effects on ENO1 protein binding to EN10 mAb (FIG. 7C and Table II). These results suggest that W301, K330 A309, E334, K335 and D300 are important for the protein-protein binding between ENO1 and EN10 mAb. These amino acid residues belong to sequences of ENO1 peptide 1, [296]FD Q D D W G A W Q K F TA[309] (FIG. 7D, SEQ ID NO:40) and peptide 2, [326] K R I A K A V N EK S[336] (FIG. 7D, SEQ ID NO:41), which may be the binding epitopes of EN10 mAb in the amino residue number from 296 to 335 (FIG. 7D; SEQ ID NO:39) of human ENO1.

a mouse non-infectious inflammation model (Ploplis, V. A. et al., (1998), Blood, 91:2005-2009).

To prove the efficacy of EN10 mAb on the inhibition of leukocyte infiltration in vivo, a mouse non-infectious inflammation (NII) model was used for the study. Twelve mice were divided into 4 groups with three mice in each group. On day one, each group was given PBS, 6 mg/kg body weight (mpk) of Enbrel, 10 mpk of mouse IgG, and 10 mpk of EN 10 mAb (ip), respectively. Two hours later, each mouse was injected with 200 microgram of casein (ip). Mice were kept at 25° C. for 12 hours. Mice were then treated with the same dose of the same drug, followed with 200 microgram of casein after two hours, respectively. Three hours latter, mouse peritoneum was opened and fluid was collected. Total peritoneum cells of each group were counted. To identify the cell population distribution of monocytes and neutrophils, peritoneum fluid cells of each group were stained with rat 1A8 antibody for neutrophils and rat anti BR1 for monocytes, visualized with FITC-conjugated goat anti-rat IgG (Jackson Lab), and analyzed with FACScan flow cytometer (Becton Dickinson). Data are presented as mean±SEM. The T-test was used to compare each group. P values <0.05 were considered statistically significant.

Figure 8A:
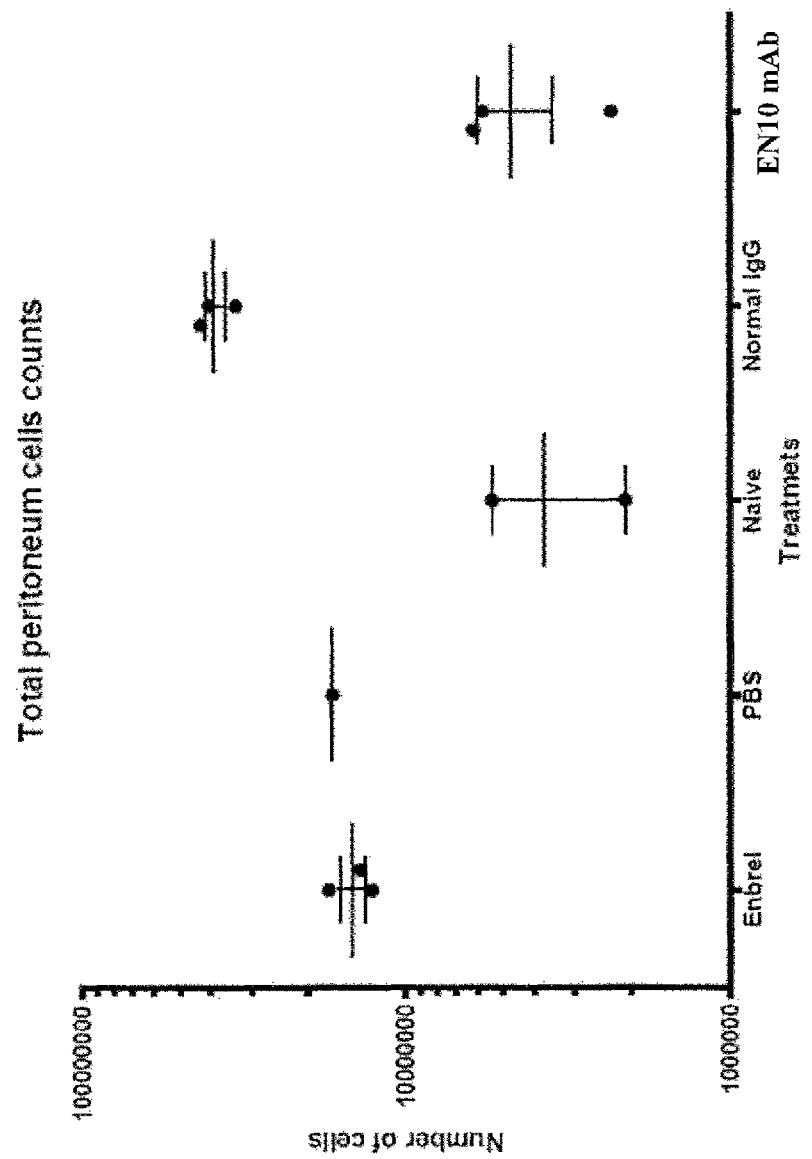
FIGS. 8A and 8B show results of inhibition of leukocyte infiltration in a mouse non-infectious inflammation model by administration of En10 mAb into mice. The detailed procedures were performed as described in Example 8.
Figure 8B:
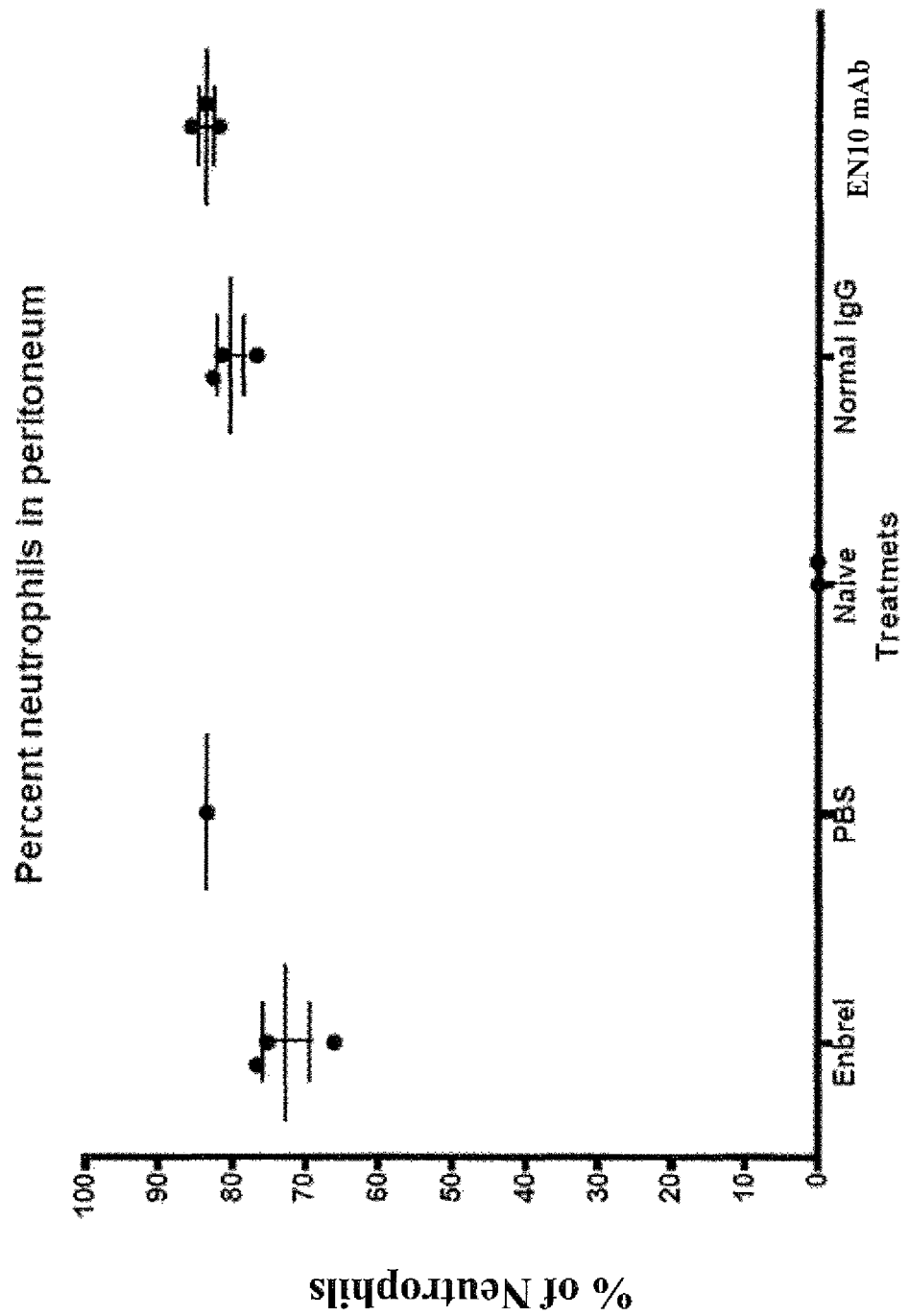

Results from this study are shown in FIG. 8A and FIG. 8B. Average total cell counts of mice treated with 6 mpk of Enbrel, vehicle, and 10 mpk of control IgG are $1.5\pm0.1\times10^7$ (N=3), $1.8\times10^7$, and $4\pm0.5\times10^7$ (N=3) in the peritoneum, respectively. However, when the same casein treated mice are given 10 mpk of EN10 mAb, the average cell counts in the peritoneum is $5\pm1.2\times10^6$ (N=3), which is significantly lower than those of Enbrel, vehicle, and the control IgG groups. No significant difference was found between the 10 mpk of EN10 mAb treated group and the naïve group ($3.9\pm1.2\times10^6$ (N=3)) (FIG. 8A)

When the cell populations in the peritoneum were analyzed, neutrophils accounts for about 73% to 85% of the total cells in the peritoneum and no significant difference was found between each group (except the naïve treatment group) in this study (FIG. 8B). This result implies that EN10 mAb can compromise the ENO1 plasminogen receptor activity, which in turn as the plasminogen-null mice decreases plasminogen activation in the tissue and prevents inflammatory cells (for example, neutrophils) from infiltrating to affected sites. Therefore, targeting ENO1 plasminogen receptor with ENO1 antibody has potential applications in the therapy of immune diseases.

TABLE II

Mutant $K_d$ Values

| Mutant | KD | Mutant | KD | Mutant | KD |
|---|---|---|---|---|---|
| Wild type | $4.43 \pm 0.65 \times 10^{-10}$ | A300 | $6.33 \pm 2.57 \times 10^{-8}$ | A301 | Non-detected |
| A302 | $3.45 \pm 0.28 \times 10^{-10}$ | A305 | $3.31 \pm 0.50 \times 10^{-10}$ | A306 | $4.65 \pm 2.42 \times 10^{-10}$ |
| A309 | $5.63 \pm 2.67 \times 10^{-9}$ | A326 | $7.87 \pm 1.35 \times 10^{-10}$ | A330 | Non-detected |
| A333 | $4.13 \pm 1.09 \times 10^{-10}$ | A334 | $1.07 \pm 4.39 \times 10^{-7}$ | A335 | $9.57 \pm 3.72 \times 10^{-9}$ |

Example 8

The results from Examples 3 and 4 suggest that EN10 mAb can compromise the ENO1 plasminogen receptor activity. This reduction of ENO1 plasminogen receptor activity in turn inhibits the activation of plasminogen, resulting in the alleviation of the invasion capability of activated U937 monocytes. This result is further supported by literature reports indicating that monocytes of plasminogen-null mice lose the migration capability and infiltration activity in Example 9

Recent literature reports indicate that monocyte infiltration is very important in the disease progression of multiple sclerosis in an EAE animal model. Based on the data in Example 8, it was hypothesized that comprising ENO1 plasminogen receptor activity by anti-ENO1 antibody will ameliorate multiple sclerosis symptoms of EAE in an animal model. Twelve seven to 10-week-old female CB57/BL/6 mice were provided subcutaneously with 100 microgram of MOG p35-55 in Freud's complete adjuvant, and then 100 ng of *pertussis* toxin was injected intra-peritoneally. Mice were randomly divided into two groups with 6 mice in each group. On the second day, each group of mice was subcutaneously injected with 200 microliter of 10 mpk of EN10 mAb and mouse IgG, respectively. On the third day, the other dose of 100 ng of *pertussis* toxin was administered intra-peritoneally. Animals were observed daily and clinical symptoms were assessed as follows: 0, no sign; 1, decreased tail tone; 2, mild monoparesis or paraesis; 3, severe paraparesis; 4, paraplegia and or quadraparesis; 5 moribund or death. All studies were performed in accordance with the guidelines prescribed by the Animal Care and Use committee at the Development center for Biotechnology, Taiwan.

Figure 9:
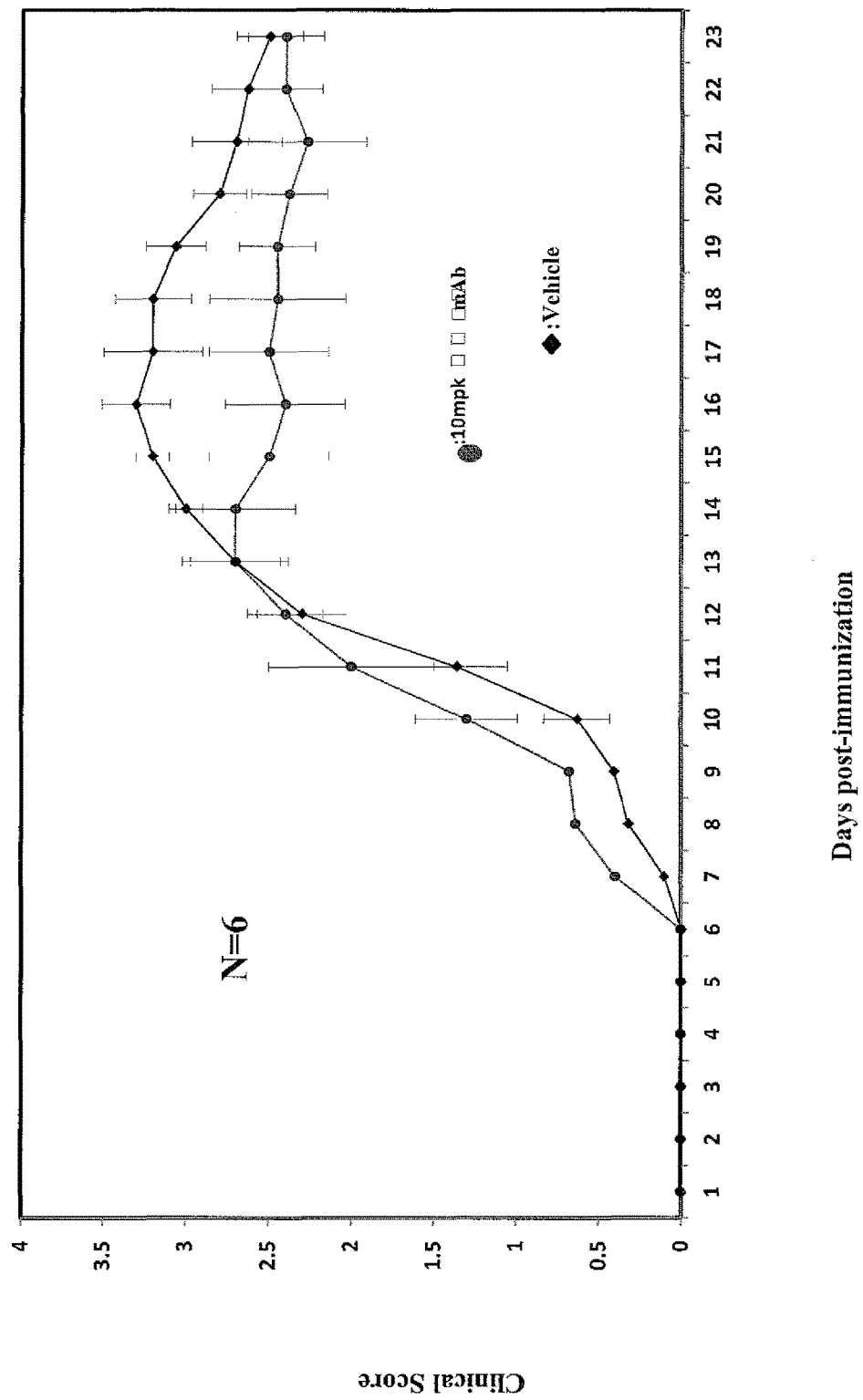
FIG. 9 shows that the administration of EN10 mAb improves the course of experimental autoimmune encephalomyelitis (EAE) in an animal prophylactic model of multiple sclerosis. The detailed procedures were performed as described in the example 9.

The results are shown in the FIG. 9. Each group of mice started to show the EAE syndromes on day 7, and there were no significant difference in clinical scores between the two groups from days 7 to day 12. In the EN10 mAb treatment group, mice reach the disease plateau on the day 13 with an average maxima clinical score of about 2.7±032 (N=6). Then, mice entered the remission phase of EAE until day 28, at which time the study was terminated. In contrast, mice treated with the mouse IgG reach the disease plateau on the day 16 with an average maxima clinical score of about 3.3±0.21 (N=6). Then, these mice started to enter the remission stage. At the end of study both groups have the same average clinical scores.

This study indicates that mouse treated with ENO1 antibody has a lower maxima clinical score of about 0.6 point on average, when compared with the IgG treatment mice. These data suggest that inhibition of ENO1 plasminogen receptor activity by antibody confers clinical benefits in the EAE mouse prophylactic model.

Example 10

In Example 9, the result indicates that administration of ENO1 antibody confers clinical benefits in the EAE mouse prophylactic model. To explore the therapeutic effects of EN10 mAb on MS, a mouse EAE therapeutic model was used in the next study. 28 seven-to 10-week-old female CB57/BL/6 mice were provided subcutaneously with 100 microgram of MOG p35-55 in Freud's complete adjuvant, and then 100 ng of *pertussis* toxin was injected intra-peritoneally. On the third day, another dose of 100 ng of *pertussis* toxin was administered. Animals were observed daily and the clinical symptoms were assessed as follows: 0, no sign; 1, decreased tail tone; 2, mild monoparesis or paraesis; 3, severe paraparesis; 4, paraplegia and or quadraparesis; 5 moribund or death. Until about day 10, at which time the average clinical score of mice was about 0.5, mice were randomly divided into 4 groups with 7 mice in each group. On days 11, 13, and 15, mice of group 1 were injected with 5 mpk of EN10 mAb intra-peritoneally. Mice of group 2 were fed daily with 15 mpk dimethyl fumarate (DMF) twice per day after day 11. Mice of group 3 were treated as those of the group 2, except that these mice were injected with 5 mpk of EN10 mAb intra-peritoneally on days 11, 13, and 15. The group 4 was the control group injected with vehicle; these mice were injected with PBS intra-peritoneally daily.

At the end of the study, the three mice with close to the average maxima clinical scores from each group were collected, and their whole bodies were perfused with the Bouin's solution. The brains and spinal cords of these mice were fixed with 10% formalin, sectioned and stained with Luxol fast blue, as well as hematoxylin and eosin (H&E). Histopathology scores of meningeal and parenchymal inflammatory lesions of demyelination were evaluated by a pathologist based on the Shackelford score method (Toxicologic Pathology, Vol 30, No 1, pp 93-96, 2002) as follows: 1, minimal; 2, slight; 3, moderate; 4, moderate/severe; 5, severe/high. Data are presented as mean±SEM. The T-test was used to compare each groups. P values <0.05 were considered statistically significant. All studies were performed in accordance with guidelines prescribed by the Animal Care and Use committee at the Development Center for Biotechnology, Taiwan.

Figure 10A:
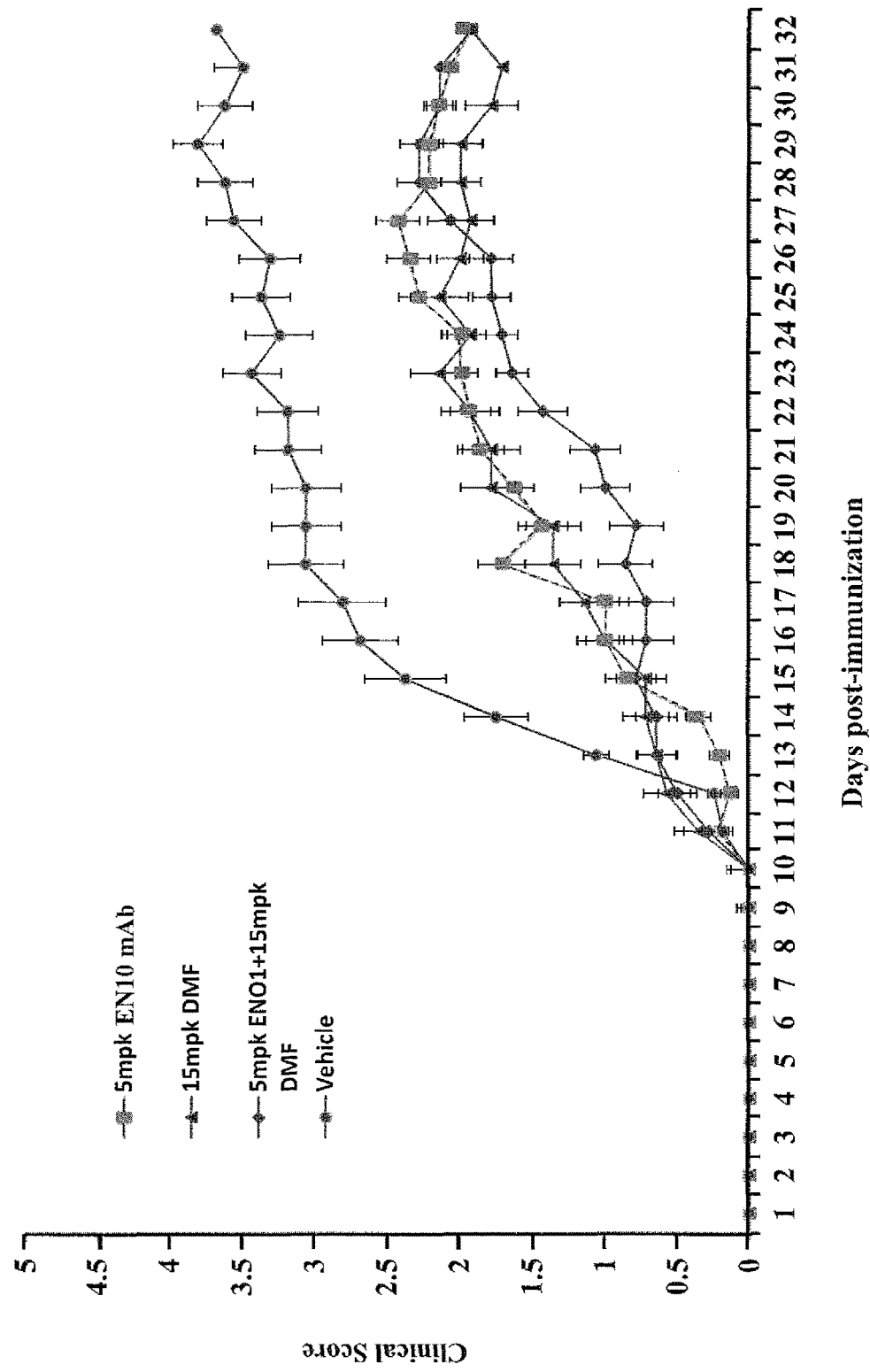
FIG. 10A shows that the administration of EN10 mAb ameliorates multiple sclerosis symptoms of EAE in an animal therapeutic model. The detailed procedures were performed as described in Example 10.

The results are shown in the Hers. 10A, 10B, 10C, and 10D. Each group of mice started to show the EAE syndromes on day 10, and at that time the average clinical score was about 0.5. After mice started to receive testing drugs on day 11, mice administered with 5 mpk EN10 mAb, 15 mpk DMF twice per day, and EN10 mAb and DMF combination, respectively, began to show slowdown in the onset of EAE syndromes. Mice in every group reach the disease plateau around day 27. At that time, the average maxima clinical scores of vehicle, 5 mpk EN10 mAb, 15 mpk DMF twice per day, and EN10 mAb and DMF combination groups are 4.1±0.34 (N=7), 2.90.16 (N=7), 2.7±0.47 (N=7), and 2.4±0.39 (N=7), respectively (FIG. 10A). The study was terminated on day 32, and 3 mice in the vehicle group died due to progression of the disease in the study period. There was no statistical difference in the average maxima clinical scores in each group, even though mice treated with 5 mpk EN10 mAb, 15 mpk DMF twice per day, and EN 10 mAb and DMF combination showed benefits of the treatments, as evidenced in the decrease in average maxima clinical scores, about 1.2, 1.4, and 1.7, respectively, as compared to that of the vehicle group.

These results indicate that inhibition of ENO1 plasminogen receptor activity by antibody showed clinical benefits in the mouse EAE therapeutic model, and three doses of 5 mpk EN10 mAb has similar efficacy as 15 mpk of DMF twice daily. Some synergistic effects were seen in the EN10 mAb and DMF combination treatment group (FIGS. 10A-10D).

To study the EAE disease benefits of mice treated with EN10 mAb and DMF, the histopathology incidences of these mouse CNS sections were further analyzed. The items analyzed include total clinical histpathology, demyelination and inflammatory scores of CNS and the tissues examined include cerebrum, cerebellum, medulla, cervical vertebrae, thoracic vertebrae, lumbar vertebrae, and sacrum. The results are shown in the FIGS. 10B, 10C, and 10D.

Figure 10B:
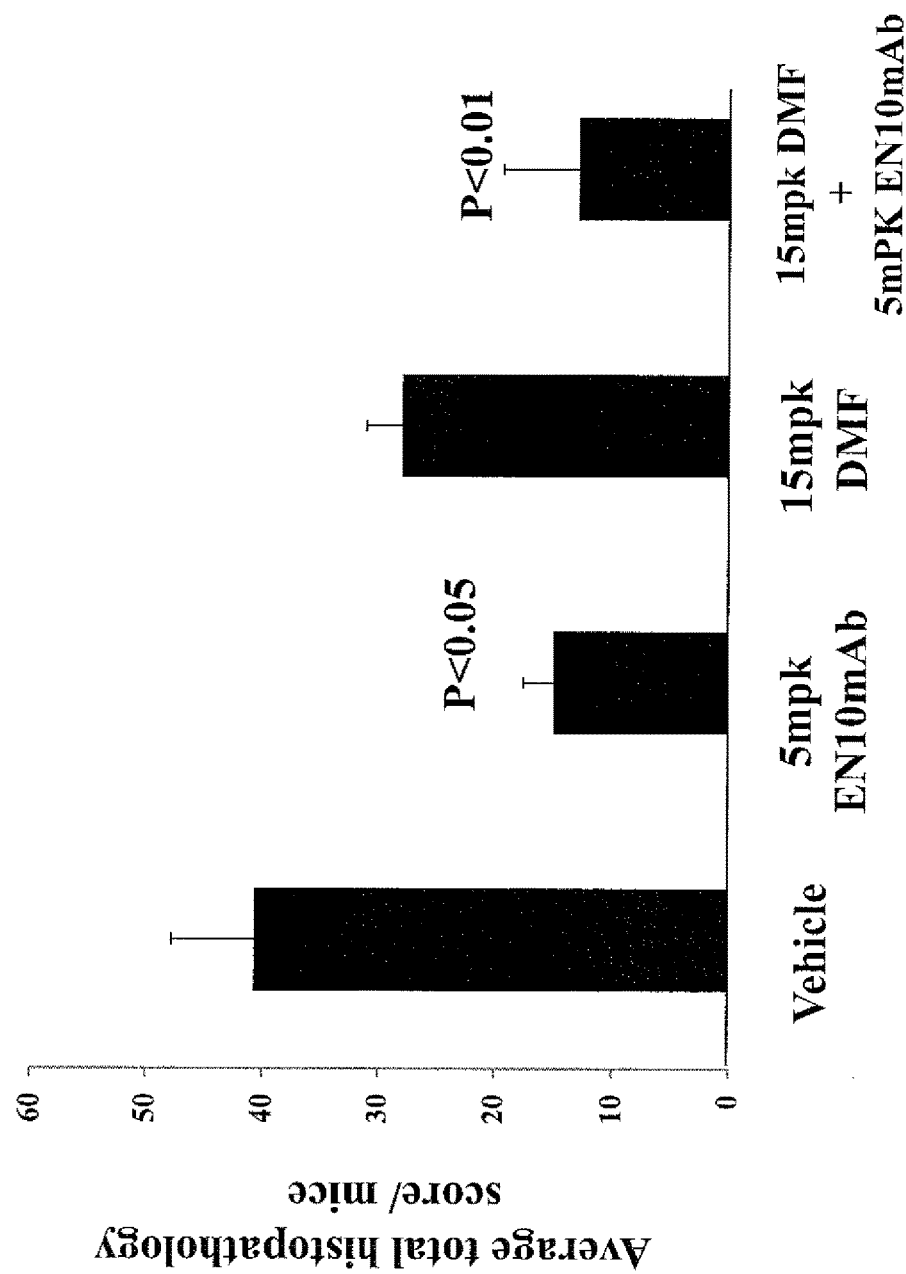
FIG. 10B shows that the administration of EN10 mAb decreases CNS histopathology scores of EAE in an animal therapeutic model. The detailed procedures were performed as described in Example 10.
Figure 10C:
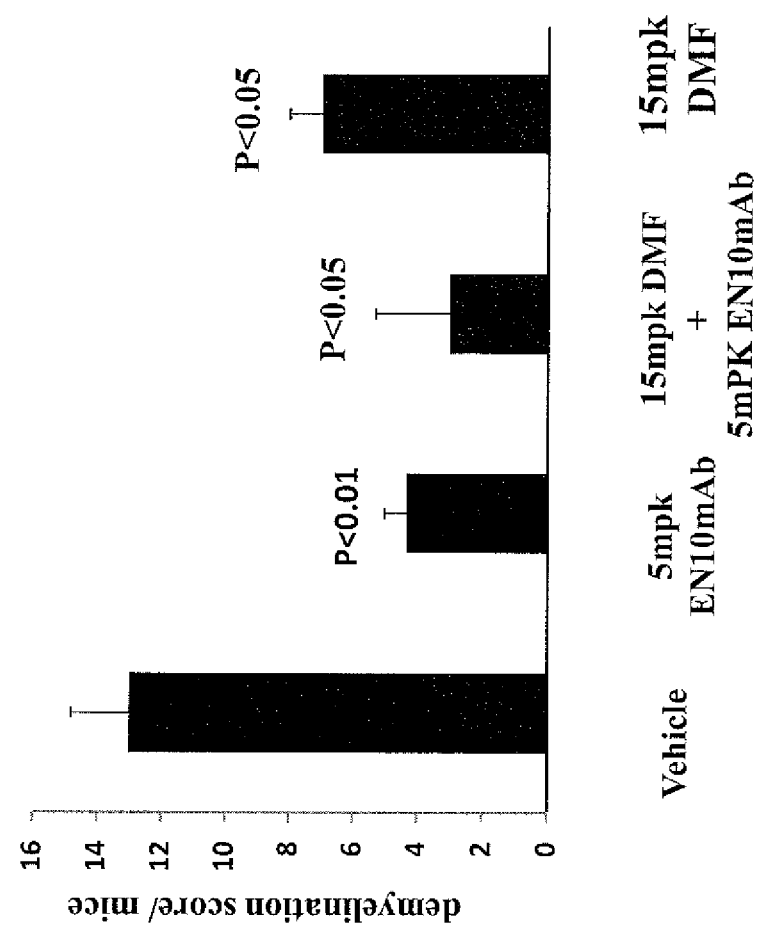
FIG. 10C shows that the administration of EN10 mAb improves CNS demyelination scores of EAE in an animal therapeutic model. The detailed procedures were performed as described in Example 10.

The average total histopathology incidence scores of mice of the vehicle, 5 mpk EN10 mAb, 15 mpk DMF twice per day, and EN10 mAb and DMF combination groups are 40.7±7.1 (N=3), 15±4.4 (N=3), 28±5.2 (N=3), and 13±11.7 (N=3), respectively. Mice in the EN10 mAb treatment group and EN10 mAb and DMF combination treatment group showed statistical difference in the average total histopathology incidence scores per mice, as compared to that of the vehicle group, with P values of 0.025 and 0.004, respectively (FIG. 10B). This result indicates that mice treated with EN10 mAb, or EN10 mAb and DMF combination have total pathology and lesions benefits on the CNS of EAE disease. When the demyelination scores of CNS were compared, results are shown in the FIG. 10C. The average total demyelination scores per mice in CNS of the vehicle, 5 mpk EN10 mAb, 15 mpk DMF twice per day, and EN10 mAb and DMF combination groups are 13±1.8 (N=3), 4.3±0.7 (N=3), 7±1.0 (N=3), and 3±2.3 (N=3), respectively. All of drug treatment groups show statistic difference in the average total demyelination incidence scores per mice in CNS, as compared to that of the vehicle group, with P values of 0.01 for the EN10 mAb group, 0.04 for the DMF group and 0.04 for the combination treatment group, respectively. This result indicates that mice treated with EN10 mAb, or DMF, or EN10 mAb and DMF combination are protected, by the drugs tested in this study, from the CNS demyelination damages in the EAE disease course. This study is further supported by literature reports that DMF has neuron protection effects on MS patients (Moharregh-Khiabani, D. et al., (2009), Current Neuropharmacology, 7:60-64; Oh, C. J. (2012) et al., PLoS ONE, 7:1-10). Three doses of 5 mpk EN10 mAb in the disease course have better efficacy than that of 30 mpk DMF daily.

Figure 10D:
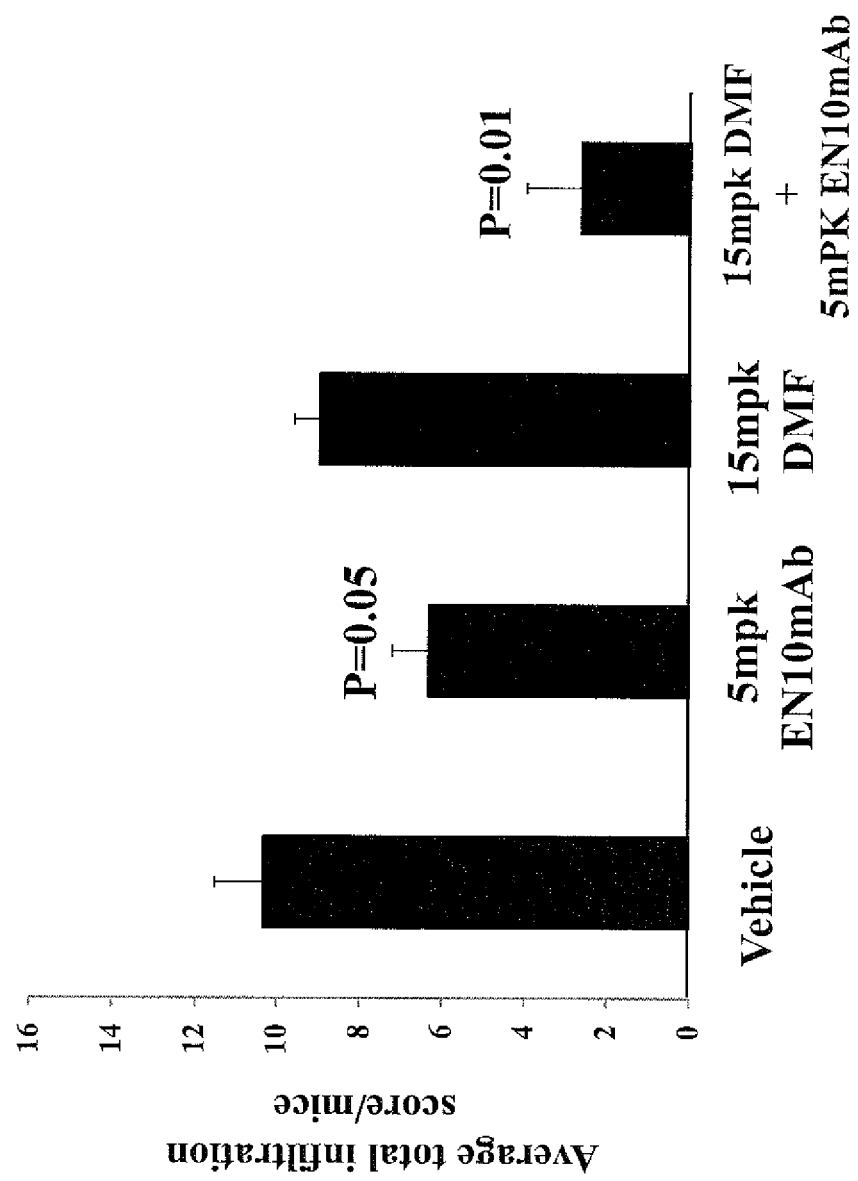
FIG. 10D shows that the administration of EN10 mAb alleviates CNS inflammation of EAE in an animal therapeutic model. The detailed procedures were performed as described in the example 10.

Leukocyte infiltration incidence score in CNS is the other parameter examined. The results are shown in FIG. 10D. The average total inflammation score per mice in CNS of the vehicle, 5 mpk EN10 mAb, 15 mpk DMF twice per day, and EN10 mAb and DMF combination groups are 10.3±1.18 (N=3), 6.3±0.9 (N=3), 9±1.0 (N=3), and 2.7±1.3 (N=3), respectively. Mice in the EN10 mAb treatment group and the EN10 mAb and DMF combination group show statistical difference in the average total inflammation score per mice in CNS, as compared to that of the vehicle group, with P values of 0.05 and 0.01, respectively (FIG. 10D). However, DMF seems to have no statistical effects in preventing inflammatory cells from entering the affected CNS sites. This result suggests that EN10 mAb or EN10 Mb combined with DMF is able to prevent leukocytes from infiltrating the CNS, thereby decreasing the pathology incidences in the CNS, more importantly to ameliorate the demyelination of CNS neuron on MS symptoms.

Example 11

Figure 11A:
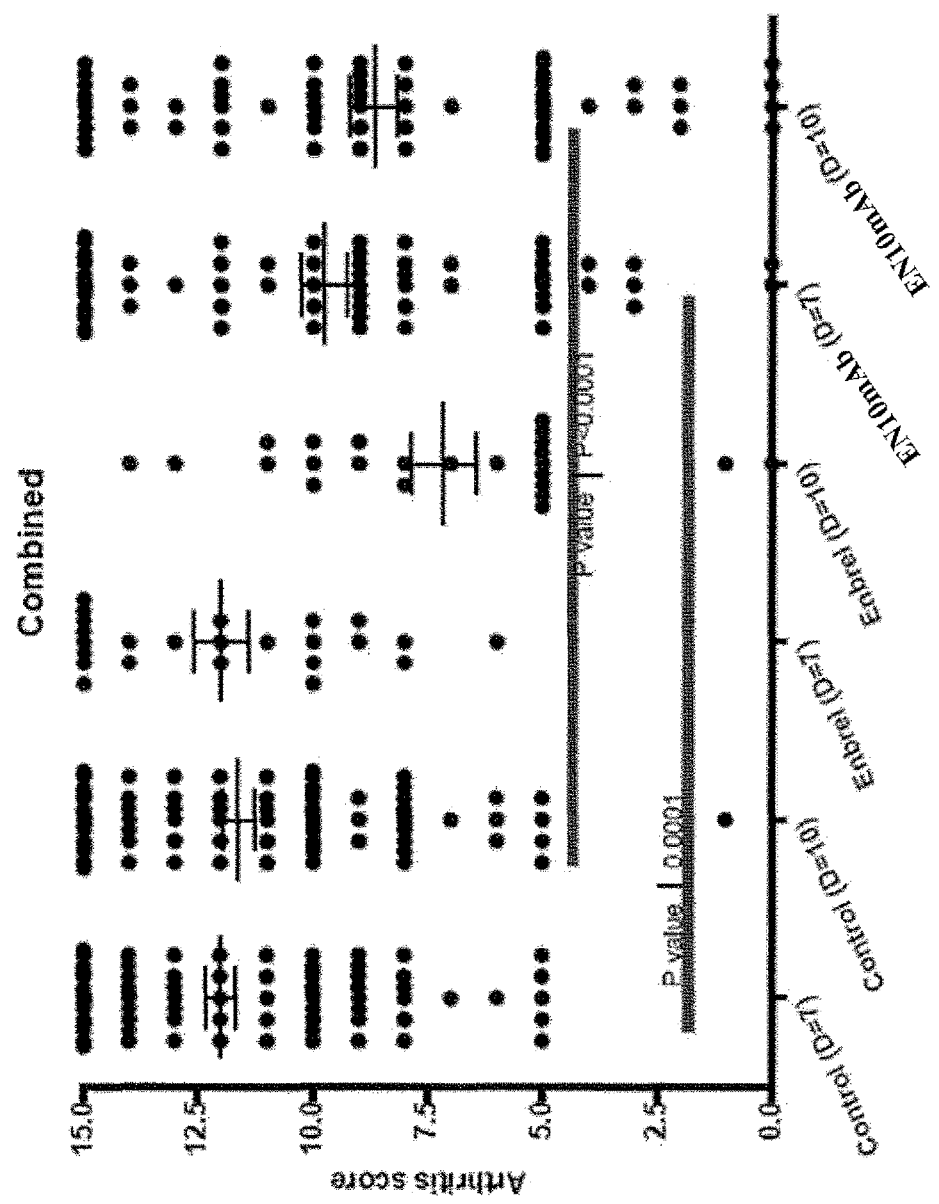
FIG. 11A shows that the administration of the EN10 mAb alleviates the symptoms of arthritis in the collagen antibody-induced arthritis rodent model. The detailed procedures were performed as described in Example 11.
Figure 11B:
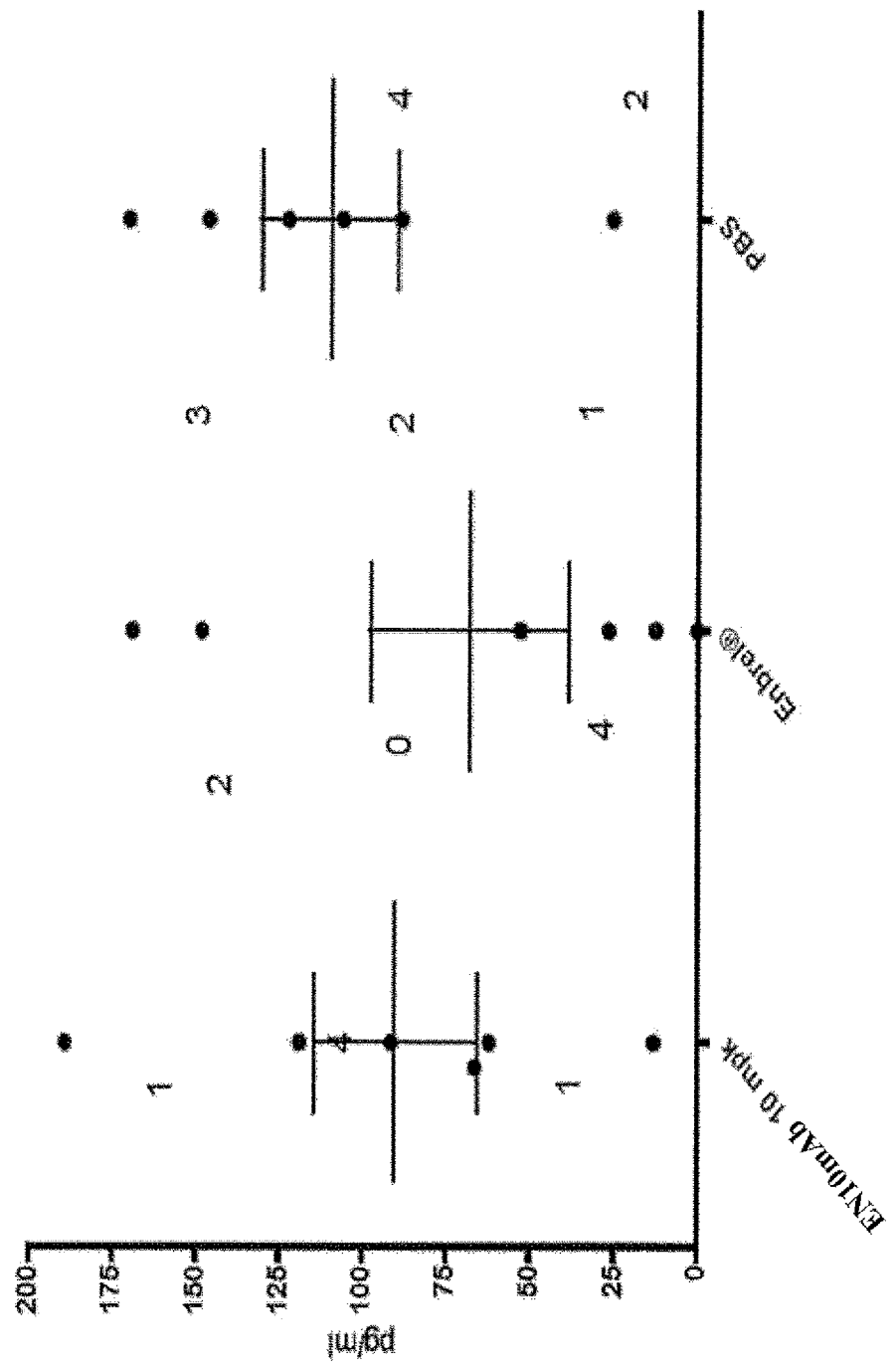
FIG. 11B shows that the treatment of the EN10 mAb down-regulates synovial IL1-b in the collagen antibody-induced arthritis rodent model. The detailed procedures were performed as described in Example 11.
Figure 11C:
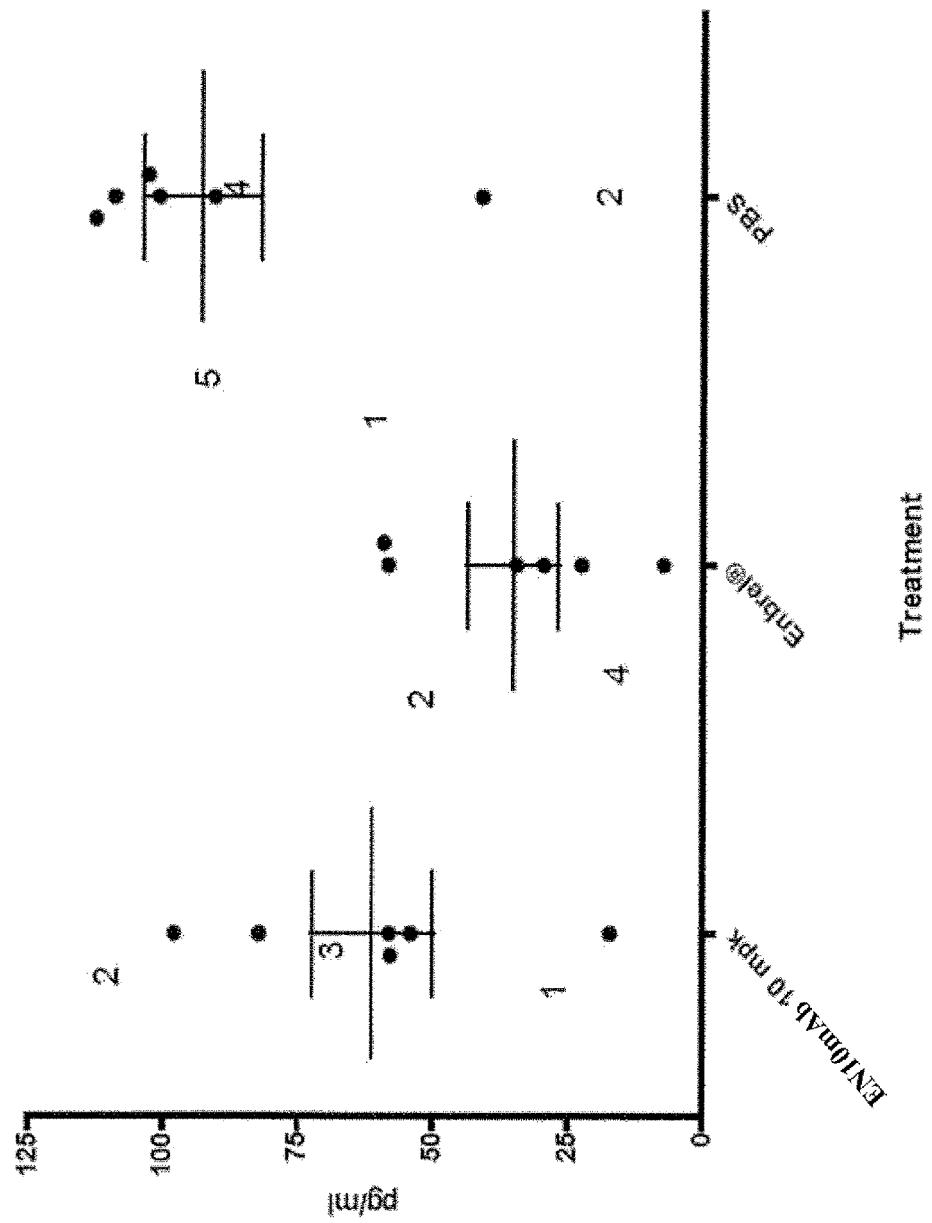
FIG. 11C show that the treatment of the EN10 mAb down-regulates synovial MMP9 in the collagen antibody-induced arthritis rodent model. The detailed procedures were performed as described in Example 11.

Bae's (Bae, S. et al. (2013) J. Immunology. 189:365-372) result shows that the activation of ENO1 plasminogen receptor activity on the surface of monocytes increases pro-inflammatory cytokines, for example TNFα and ILβ, in the Rheumatoid arthritis (RA) patient's PBMC and results in the exacerbation of diseases. When the epitope of antibody used by Bae's study is compared with EN10 mAb, we found that EN10 mAb binds to a different epitope from that of Bae's study. The epitope of anti human ENO1 used in Bae's study locates at N-terminal and center part of ENO1 protein. However, the epitope of EN10 mAb is at amino acid residues from 296 to 336. Two antibodies show the different plasminogen receptor agonist discrepancy. The antibody used in Bae's study displays the agonist activity, which activates the plasminogen receptor activity of ENO1. However, EN10 mAb shows antagonist activity when the antibody was administrated in the stimulated human monocytes. This study supports our MS results in Examples 8, 9, and 10 and Presslor' study in the lung inflammatory model that down-regulating of ENO1 plasminogen receptor activity on monocytes prevents activated monocytes from infiltrating to the inflammation sites. Both results suggest that the therapeutic effect of ENO1 antibodies in immune diseases is epitope-dependent and some of ENO1 antibodies, such as the one used in Bae's study, may result in the exacerbation of diseases. To confirm our EN10 mAb efficacy in RA, a study was performed using a collagen antibody-induced arthritis rodent model. Six week-old Balb/c male mice were injected with 1.5 mg/mice of mouse monoclonal anti-type II collagen intravenously. Four days later, mice were treated with 50 microgram/mice of LPS (*E. coli* 0111B4) intraperitoneally. Mice were divided into 3 groups with three mice in each group. Each group was treated with 5 mpk of mouse IgG, 5 mpk of EN10 mAb, and 6 mpK of Enbrel, respectively, on days 1, 3, 5, and 7. Animals were observed daily and clinical symptoms were assessed as follows: body weight (everyday), footpad thickness (day 1, 3, 7, and 10), arthritis score (day 3, 7, and 10), pathology (day 10), and cytokines (ELISA). Data are presented as mean±SEM. ANOVA followed by Newman-Keuls multiple comparison test was used to compare three or more groups. P values <0.05 were considered statistically significant. All studies were performed in accordance with the guidelines prescribed by the Animal Care and Use committee at the Development center for Biotechnology, Taiwan. For the cytokine analysis, knees were opened, and synovial fluid was washed with PBS and collected. The cytokine concentrations were analyzed with a Cytokine ELISA kit The result shows in the FIG. 11A. On the day 7 the average arthritis scores of 10 mpK of EN10 mAb, 6 mpk of Enbrel, and vehicle groups are 10±0.54 (N=3), 12±0.8 (N=3) and 12±0.3 (N=3), respectively. The average arthritis score of mice treated with EN10 mAb is statistically different from that of the vehicle group with a P value of 0.0001. On the day 10, the average arthritis scores of 10 mpK of EN10 mAb, 6 mpk of Enbrel and vehicle groups are 8.9±0.53 (N=3), 7.2±0.8 (N=3) and 11.7±0.3 (N=3), respectively. The average arthritis score of mice treated with EN10 mAb and 6 mpk of Enbrel are statistically different from that of the vehicle group with a P value of less than 0.0001 (FIG. 11A). The results from this study indicate that compromising ENO1 plasminogen receptor activity with EN 10 mAb reduced the symptoms of RA in the CAIA rodent model. When the IL1b and MMP9 cytokines were analyzed in the synovial fluid of CAIA mice, the average MMP9 concentrations of the EN10 mAb treated, Enbrel treated, and vehicle groups are 62.5±5, 34±9.4, and 92.5±11.25 ng/ml (N=3). For the IL1b cytokine, the average concentrations of the EN10 mAb treated, Enbrel treated, and vehicle groups are 91±15.8, 68.9±31, and 115.6±20 pg/ml (N=3), respectively. Both cytokines are down-regulated in the EN10 mAb and Enbrel treated groups. Based on the results shown in FIGS. 11A, 11B and 11C, it can be concluded that in both cases, three doses of 10 mpk EN 10 mAb and Enbel have therapeutic effects in the reduction of the symptoms of RA.

Example 12

Result from examples 9, 10, and 11 suggest that compromising ENO1 activity by an ENO1 antagonist antibody alleviates the syndromes of MS and Rheumatoid arthritis in mouse EAE and CAIA models.

We hypothesize that the similar epitope of mouse ENO1 is effective on similar mouse auto immune diseases. 10 mg of mouse ENO1 protein was contracted to generate rat anti mouse ENO1 antibody by Genescript Inc. (Piscataway, N.J., USA). To screen for hybridomas that secreted rat anti mouse ENO1 antibody, four hundred nanogram of mouse ENO1 protein was coated on a 96-well ELISA plate, and the plate was further washed with PBS. Serial dilutions from each hybridoma supernatant were added to the plate, and the plate was incubated at 37° C. for 1 hour. A goat anti-rat IgG conjugated with hypoxanthine phosphoribosyltransferase assay (HPRT) was added. After 1 hour, 3,3',5,5'-Tetramethylbenzidine (TMB) was added and OD405 was read. 75 positive clones out of 30,000 hybridomas with significant mouse ENO1 binding affinities were further subjected to do the EN10 mAb competition assay (FIG. 12A). An ELISA plate coated with mouse ENO1 protein was used to bind the individual supernatants (about 100 micro liter) of positive hybridomas clones. After the plate was washed trice with PBS, 100 nanogram of EN10 mAb was added to the plate, and the plate was incubated at 37°c for one hour. A goat anti-rat IgG conjugated with hypoxanthine phosphoribosyltransferase assay (HPRT) was added. After 1 hour, 3,3',5, 5'-Tetramethylbenzidine (TMB) was added and OD405 was read. The result shows in the FIG. 12B. Only 5 of 75 hybridoma supernatants have mouse ENO1 binding activities competed by EN10 mAb. This result suggests that these 5 rat anti mouse ENO1 antibodies may have the similar epitope in the mouse ENO1 to that of EN10 mAb in the human ENO1.

Example 13

To evaluate the mouse ENO1 binding affinity of 5 anti-mouse ENO1 antibodies, the hybridomas were grown in 25 ml of SFM medium (Gibco Inc). After one week culture, individual supernatant was collected. The antibody was further purified by 40% ammonium sulfate and Protein A column (Montage antibody purification kit Millipore). The purified antibody was concentrated with an Amicon Ultra-15 centrifugal filter device, following the protocols provided by the manufacturer (Millpore Inc).

Four hundred nanogram of mouse ENO1 protein was coated on a 96-well ELISA plate, and the plate was further washed with PBS. Serial dilutions from $1 \times 10^{-12}$ to $1 \times 10^{-8}$ M of individual antibody were added to the plate, and the plate was incubated at 370 C for 1 hour. A goat anti-rat IgG conjugated with hypoxanthine phosphoribosyltransferase (HPRT) was added. After 1 hour, 3,3',5,5'-Tetramethylbenzidine (TMB) was added and OD405 was read. Every study was repeated three times. Data were presented as mean±SD. OD readings and concentrations of antibodies were used to make a multiple scatter plot using Sigmaplot. The Kd values were predicted by four parameter logistic fit.

Figure 13:
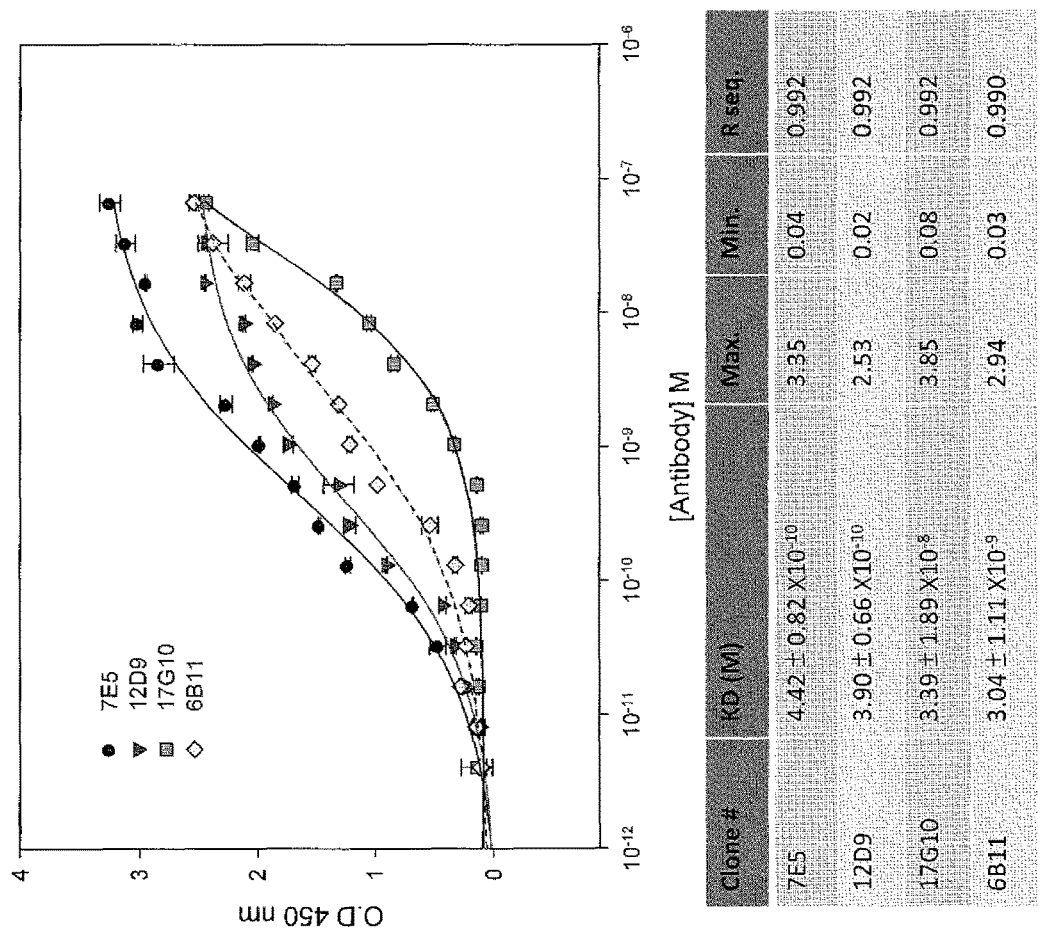
FIG. 13. shows ELISA results from ENO1 binding by 5 rat anti mouse ENO1 antibodies isolated from the supernatants of individual hybridoma. Ammonium sulfate purification, and protein A column purification were performed as described in Example 1. These data show the Kd of rat anti mouse ENO1 7E5

The results of this experiment are shown in FIG. 13. The Kd value of individual antibodies range from $3.90 \pm 0.66 \times 10^{-10}$ M (N=3) to $3.39 \pm 1.89 \times 10^{-8}$ M (N=3). Due to the low productivity of clone 12D9, 7E5 was chosen to do the further study.

Example 14

In Examples 9 and 10, the result indicates that administration of ENO1 antibody confers clinical benefits in the EAE mouse prophylactic and therapeutic models. To explore whether 7E5 has the similar therapeutic effects of EN10 mAb on MS, a mouse EAE therapeutic model was used in the next study. 18 seven-to-10-week-old female CB57/BL/6 mice were provided subcutaneously with 100 microgram of MOG p35-55 in Freud's complete adjuvant, and then 100 ng of *pertussis* toxin was injected intra-peritoneally. On the third day, another dose of 100 ng of *pertussis* toxin was administered. Animals were observed daily and the clinical symptoms were assessed as follows: 0, no sign; 1, decreased tail tone; 2, mild monoparesis or paraesis; 3, severe paraparesis; 4, paraplegia and or quadraparesis; 5 moribund or death. Until about day 10, at which time the average clinical score of mice was about 0.5, mice were randomly divided into 3 groups with 6 mice in each group. On days 11, 13, and 15, mice of group 1 were injected with 5 mpk of 7E5 mAb subcutaneously. Mice of group 2 were injected with 20000 units of Betaferon subcutaneously. The group 3 was the control group injected with PBS vehicle subcutaneously.

At the end of the study, the three mice with close to the average maxima clinical scores from each group were collected, and their whole bodies were perfused with the Bouin's solution. The brains and spinal cords of these mice were fixed with 10% formalin, sectioned and stained with Luxol fast blue, as well as hematoxylin and eosin (H&E). Histopathology scores of meningeal and parenchymal inflammatory lesions of demyelination were evaluated by a pathologist based on the Shackelford score method (Toxicologic Pathology, Vol 30, No 1, pp 93-96, 2002) as follows: 1, minimal; 2, slight; 3, moderate; 4, moderate/severe; 5, severe/high. Data are presented as mean±SEM. The T-test was used to compare each groups. P values <0.05 were considered statistically significant. All studies were performed in accordance with guidelines prescribed by the Animal Care and Use committee at the Development Center for Biotechnology, Taiwan.

Figure 14A:
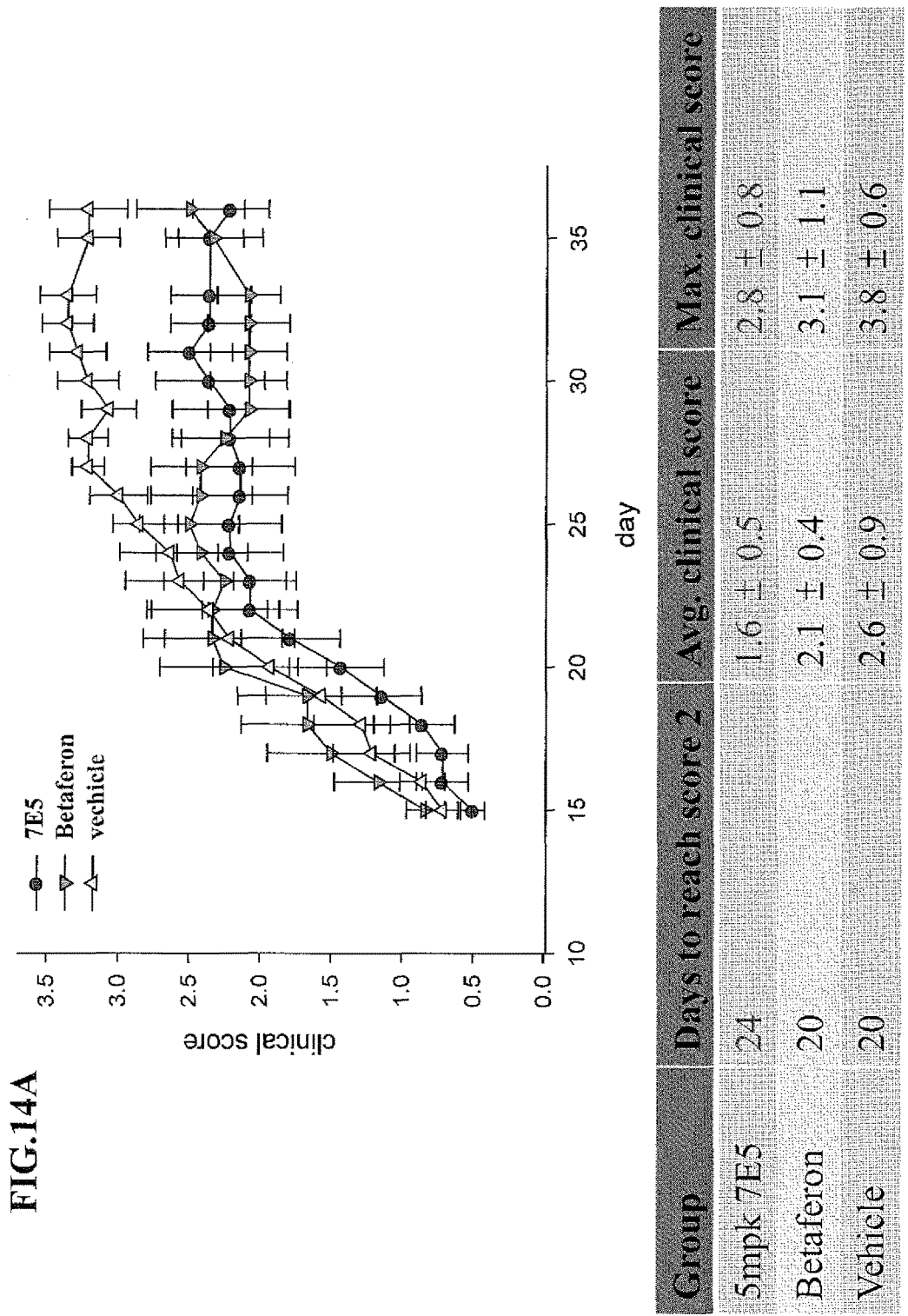
FIG. 14A. shows that administration of rat anti mouse ENO1 antibody 7E5 ameliorates multiple sclerosis symptoms of EAE in an animal therapeutic model. The detailed procedures were performed as described in Example 14.

The results are shown in the FIGS. 14A, 14B, 14C, and 14D. Each group of mice started to show the EAE syndromes on day 10, and at that time the average clinical score was about 0.5. After mice started to receive testing drugs on day 11, mice administered with 5 mpk 7E5 mAb, and 20000 units of Betaferon, respectively, began to show slowdown in the onset of EAE syndromes. Mice in every group reach the disease plateau around day 27. At that time, the average maxima clinical scores of vehicle, 5 mpk 7E5 mAb, and 20000 units of Betaferon groups are 2.6±0.9 (N=6), 1.6±0.5 (N=6), and 2.1±0.4 (N=6), respectively (FIG. 14A). There was no statistical difference in the average maxima clinical scores in each group, even though mice treated with 7E5 mAb, and 20000 units of Betaferon showed benefits of the treatments, as evidenced in the decrease in average maxima clinical scores, about 1.0, and 0.5, respectively, as compared to that of the vehicle group. These results indicate that 7E5 antibody has the similar inhibition of ENO1 plasminogen receptor activity as that of EN 10 mAb showed clinical benefits in the mouse EAE therapeutic model, even though they bind to different species of ENO1 with similar epitope.

To study the EAE disease benefits of mice treated with 7E5 mAb and Betaferon, the histopathology incidences of these mouse CNS sections were further analyzed. The items analyzed include total clinical histpathology, demyelination and inflammatory scores of CNS and the tissues examined include cerebrum, cerebellum, medulla, cervical vertebrae, thoracic vertebrae, lumbar vertebrae, and sacrum. The results are shown in the FIGS. 14B, 14C, and 14D.

Figure 14B:
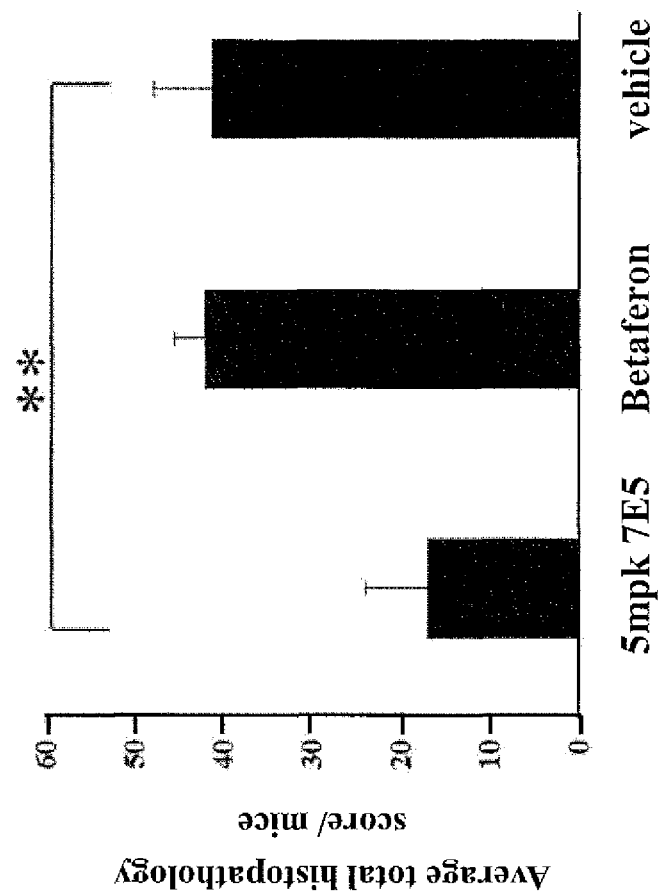
FIG. 14B shows that the administration of rat anti mouse ENO1 antibody 7E5 decreases CNS histopathology scores of EAE in an animal therapeutic model. The detailed procedures were performed as described in Example 14.
Figure 14C:
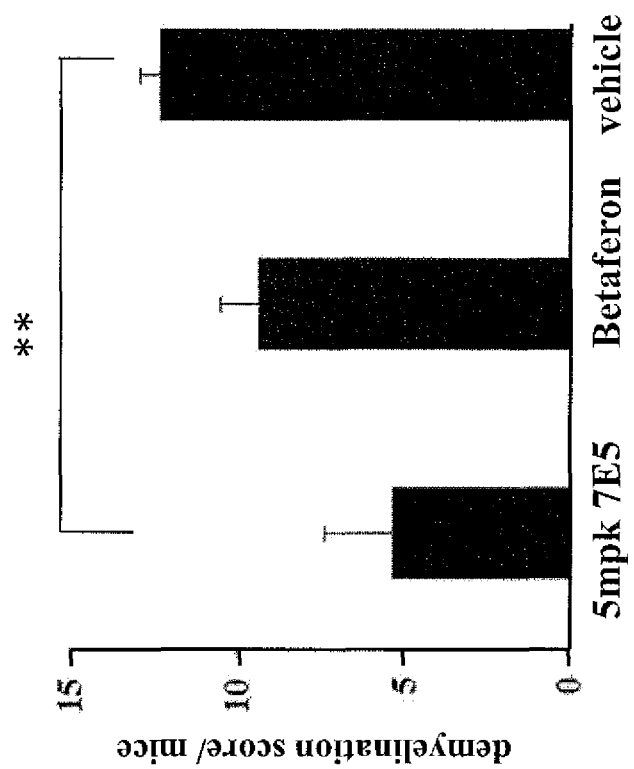
FIG. 14C shows that the administration of rat anti mouse ENO1 antibody 7E5 improves CNS demyelination scores of EAE in an animal therapeutic model. The detailed procedures were performed as described in Example 14.

The average total histopathology incidence scores of mice of the vehicle, 5 mpk 7E5 mAb, and 20000 units of Betaferon groups are 40.7±6.8 (N=3), 14.7±9. (N=3), and 41.8±3.4 (N=3), respectively. Mice in the 7E5 mAb treatment group showed statistical difference in the average total histopathology incidence scores per mice, as compared to that of the vehicle group, with P values of 0.025 (FIG. 14B). This result indicates that mice treated with 7E5 mAb have total pathology and lesions benefits on the CNS of EAE disease. When the demyelination scores of CNS were compared, results are shown in the FIG. 14C. The average total demyelination scores per mice in CNS of the vehicle, 5 mpk 7E5 mAb, and 20000 units of Betaferon groups are 12.2±0.8 (N=3), 5.1±1.4 (N=3) and 9.1±1.1(N=3), respectively. The 7E5 mAb group shows statistic difference in the average total demyelination incidence scores per mice in CNS, as compared to that of the vehicle group, with P values of 0.01. This result indicates that mice treated with 7E5 mAb are protected, by the drugs tested in this study, from the CNS demyelination damages in the EAE disease course.

Figure 14D:
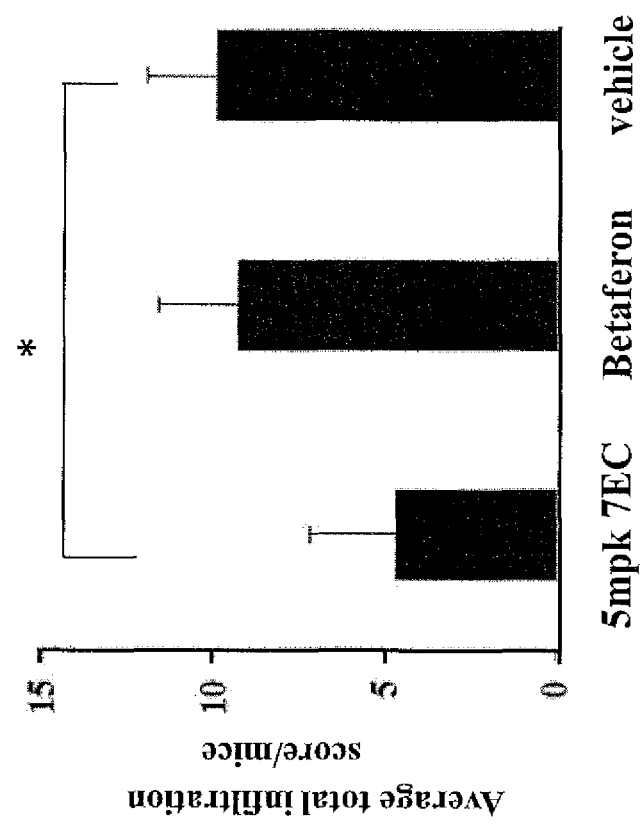
FIG. 14D shows that the administration of rat anti mouse ENO1 antibody 7E5 alleviates CNS inflammation of EAE in an animal therapeutic model. The detailed procedures were performed as described in the example 14.

Leukocyte infiltration incidence score in CNS is the other parameter examined. The results are shown in FIG. 14D. The average total inflammation score per mice in CNS of the vehicle, 5 mpk 7E5 mAb, and 20000 units of Betaferon groups are 10.±1.9 (N=3), 4.6±2.7 (N=3), and 9.2±2.6 (N=3), respectively. Mice in the 7E5 mAb treatment group shows statistical difference in the average total inflammation score per mice in CNS, as compared to that of the vehicle group, with P values of 0.05 (FIG. 14D). However, Betaferon seems to have no statistical effects in preventing inflammatory cells from entering the affected CNS sites. This result suggests that the same as EN10 mAb 7E5 mAb is able to prevent leukocytes from infiltrating the CNS, thereby decreasing the pathology incidences in the CNS, more importantly to ameliorate the demyelination of CNS neuron on MS symptoms. Our results suggests that the peptide region of human ENO1 from amino acid number 296 to 336 (SEQ ID NO:39) including peptide sequences FDQDDWGA WQKFTA (SEQ ID NO:40) and KRI-AKAVNEKS (SEQ ID NO:41) are very important for an antibody to inhibit the plasminogen receptor activity and as a therapeutic agent to treat immune monocyte relative immune diseases, even in the mice the MOA is effective.

Results from Examples 9, 10 11 and 14 indicate that inhibition of ENO1 plasminogen receptor activity by ENO1 antibodies, regardless species, can decrease plasminogen activation, inhibit the UPAS cascade, and reduce the degradation of extracellular matrix activity. As a result, infiltration of inflammatory monocytes to damage affected cells is inhibited, and this inhibition ameliorates the symptoms of inflammations in NII, MS in EAE, and RA in CAIA models. Therefore, targeting ENO1 plasminogen receptor on the surface of activated cells (such as monocytes) can be used to treat inflammatory diseases, and the ENO1 antibody against the peptide region of human ENO1 from amino acid number 296 to 336 (SEQ ID NO:39) including peptide sequences FDQDDWGA WQKFTA (SEQ ID NO:40) and KRI-AKAVNEKS (SEQ ID NO:41) is useful as a therapeutic drug for the immune disease patients.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An antibody, or an scFv, Fab or F(ab)2 fragment thereof, wherein the antibody, or the scFv or Fab or F(ab)2 fragment thereof, can bind to an epitope on human ENO1 and inhibit ENO1 plasminogen receptor activity, wherein the epitope is located in a region consisting of the sequence of 296FDQDDWGAWQKFTASAGIQVVGDDLTVTNPK RIAKAVNEKS336 (SEQ ID NO:39) of human ENO1.

2. The antibody, or an scFv, Fab or F(ab)2 fragment thereof, according to claim 1, wherein the epitope is located in a region consisting of the sequence of 296FDQDDW-GAWQKFTA 309 (SEQ ID NO:40) or 326KRI-AKAVNEKS336 (SEQ ID NO:41) of human ENO1.

3. The antibody, or the scFv, Fab or F(ab)2 fragment thereof, according to claim 1, wherein the antibody is a monoclonal antibody.

4. A pharmaceutical composition for treating an inflammatory disease or an immune disorder, comprising the antibody, or the scFv, Fab or F(ab)2 fragment thereof, according to claim 1 and a pharmaceutically acceptable carrier.

5. A method for treating an inflammatory disease or an immune disorder, comprising administering to a subject in need thereof the antibody, or an scFv, Fab or F(ab)2 fragment thereof, according to claim 1 an antagonist against ENO1, wherein the antagonist binds ENO1 and inhibits ENO1 plasminogen receptor activity.

6. The method of claim 5, wherein the subject is human and the anti-ENO1 antibody binds human ENO1 protein.

7. The method of claim 6, wherein the anti-ENO1 antibody inhibits a plasminogen receptor activity of the human ENO1 protein by preventing plasminogen from binding to the human ENO1 protein.

8. The method of claim 5, wherein the anti-ENO1 antibody is a monoclonal antibody.

9. The method of claim 5, wherein the inflammatory disease or immune disorder is multiple sclerosis, rheumatoid arthritis, Crohn's disease, ulcerative colitis, systemic Lupus erythematosus, chronic obstructive pulmonary disease (COPD), asthma, allergy, psoriasis, type 1 diabetes mellitus, atherosclerosis or osteoporosis.

10. The method of claim 9, wherein the anti-ENO1 antibody is a monoclonal antibody.

11. The method of claim 10, wherein the anti-ENO1 antibody binds human ENO1 with a Kd of 1×10-7M or less.

12. The method of claim 5, wherein the anti-ENO1 antibody is selected from the group consisting of a chimeric antibody, a humanized antibody, an affinity matured antibody, a human antibody, a bispecific antibody and antibody drug conjugated (ADC).

13. The method of claim 5, wherein the anti-ENO1 antibody can specifically bind to an ENO1 plasminogen receptor of monocytes or leukocytes.

14. The method of claim 5, further comprising administering to the subject in need thereof an immune-suppressor immune-suppression modulator.

15. The method according to claim 5, wherein the epitope is located in a region consisting of the sequence of 296FDQDDWGAWQKFTA309 (SEQ ID NO:40) or 326KRIAKAVNEKS336 (SEQ ID NO:41) of human ENO1.

* * * * *